United States Patent [19]
Weiss

[11] Patent Number: 5,840,708
[45] Date of Patent: Nov. 24, 1998

[54] ADMINISTRATION OF OLIGONUCLEOTIDES ANTISENSE TO DOPAMINE RECEPTOR MRNA FOR DIAGNOSIS AND TREATMENT OF NEUROLOGICAL PATHOLOGIES

[75] Inventor: Benjamin Weiss, Wynnewood, Pa.

[73] Assignee: Allegheny University of the Health Sciences, Philadelphia, Pa.

[21] Appl. No.: 448,386

[22] PCT Filed: Dec. 14, 1993

[86] PCT No.: PCT/US93/12161

§ 371 Date: Jun. 7, 1995

§ 102(e) Date: Jun. 7, 1995

[87] PCT Pub. No.: WO94/13303

PCT Pub. Date: Jun. 23, 1994

Related U.S. Application Data

[63] Continuation-in-part of Ser. No. 991,582, Dec. 14, 1992, abandoned.

[51] Int. Cl.$^6$ .............................. A01N 43/04; C07H 21/04
[52] U.S. Cl. .......................... 514/44; 536/24.5; 536/24.3; 536/24.31; 536/24.33; 536/325; 536/352; 536/353; 536/366; 435/6; 435/172.3; 435/320.1; 435/375; 424/417; 424/450; 935/6; 935/8; 935/34; 935/76
[58] Field of Search .............................. 514/44; 536/24.5, 536/24.3, 24.31, 24.33; 935/6, 8, 34, 76; 435/6, 172.3, 240.2, 320.1, 375, 325, 352, 353, 366; 424/450, 417

[56] References Cited

FOREIGN PATENT DOCUMENTS

WO9005780  5/1990  WIPO.
WO9200986  1/1992  WIPO.

OTHER PUBLICATIONS

Crystal et al. (1995) Science 270: 404–410.
B. Weiss et al., Neurochemical Pharmacology—A Tribute to B.B. Brodie, E. Costa, ed., Raven Press, Ltd., New York, pp. 149–164 (1989).
D. Sibley et al., Trends in Pharmacological Sciences, 13: 61–69 (1992).
P.E. Settler et al., Eur. J. Pharmacol., 50: 419–430 (1978).
K. Tsuruta et al., Nature, 292: 463–465 (1981).
P. Sokoloff et al., Nature, 347: 146–151 (1990).
K. Nicklaus et al., J. of Pharmacol. Exp. Ther., 247: 343–348 (1988).
D. Hoyer et al., Eur. J. Pharmacol., 150: 181–184 (1988).
H. Van Tol et al., Nature, 358: 149–152 (1992).
E. Uhlmann et al., Chemical Review, 90: 544–584 (1990).
M. Simons et al., Nature, 359: 67–70 (1992).
R. Burch et al., J. Clin. Invest., 88: 1190–1196 (1991).
K. Mack et al., J. Neurochem., 57: 795–801 (1991).
D. Grandy et al., Proc. Natl. Acad. Sci. USA, 86: 9762–9766 (1989).
H. Van Tol et al., Nature 350: 610–614 (1991).
Q. Zhou et al., Nature, 347: 76–80 (1990).
R. Sunahara et al., Nature, 350: 614–619 (1991).
A. Dearry et al., Nature, 347: 72–76 (1990).
M. Minowa et al., Proc. Natl. Acad. Sci. USA, 89: 3045–3049 (1992).
S. Agrawal et al., Proc. Natl. Acad. Sci. USA, 88: 7595–7599 (1991).
P.S. Miller et al., Anti–Cancer Drug Design, 2: 117–128 (1987).
C. Bennett et al., Mol. Pharmacol., 41: 1023–1033 (1992).
S.L. Loke et al., Current Topics Microbiol. Immunol., 141: 282–289 (1988).
J. Connor et al., Cancer Res., 46: 3431–3435 (1986).
R. Iyer et al., J. Am. Chem. Soc., 112: 1253–1254 (1990).
E. Uhlmann et al. Chemical Reviews 90(4): 543–584 ('90).
P. Westermann et al. Biomed. Biochim. Acta 48(1): 85–93 ('89).
W. James Antirival Chem. & Chemotherapy 2(4): 191–214 ('91).
J. Milligan et al. J. Med. Chem. 36(14):1923–1937 ('93).
B. Tsang et al., Cancer Gene Therapy 1(1): 65–71 ('94).
C. Stein et al., Science 261: 1004–12 ('93).

*Primary Examiner*—Christopher S. F. Low
*Attorney, Agent, or Firm*—Dann Dorfman Herrell and Skillman

[57] ABSTRACT

A method and pharmaceutical preparation are provided for diagnosing and treating pathological conditions related to a dopamine receptor abnormality. The method comprises administering to a patient having such a pathological condition an oligonucleotide antisense to one or more RNA molecules encoding one of the several dopamine receptors. The antisense oligonucleotides bind specifically to expression-controlling sequences of such RNA molecules, thereby selectively controlling expression of one or more dopamine receptor subtypes, and alleviating the pathological conditions related to their expression.

27 Claims, 17 Drawing Sheets

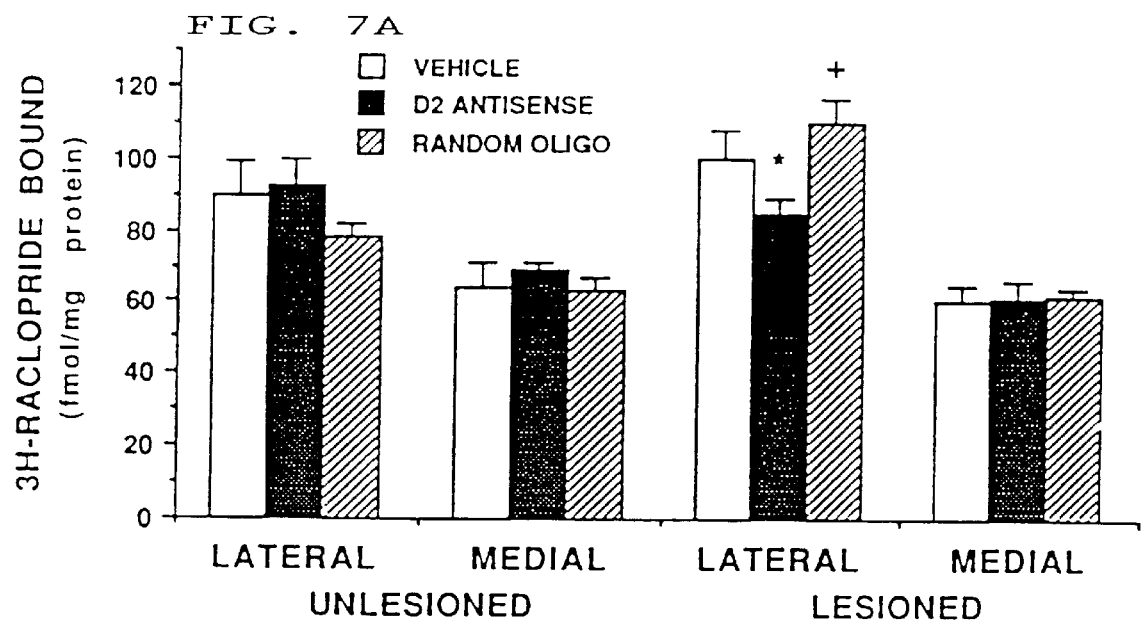
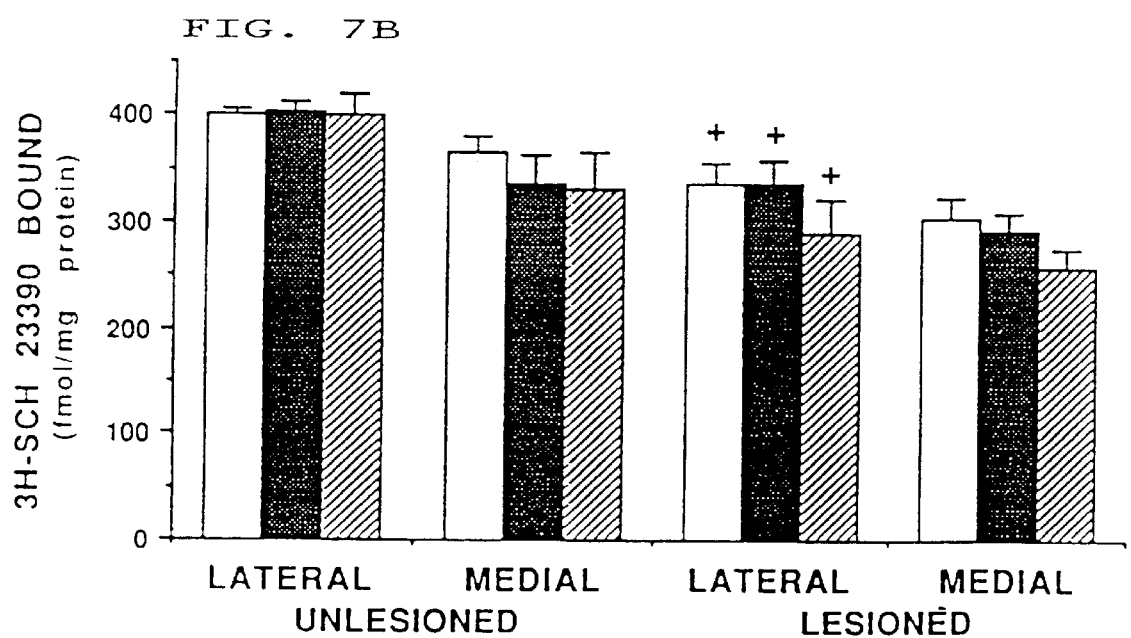

ADMINISTRATION OF OLIGONUCLEOTIDES ANTISENSE TO DOPAMINE RECEPTOR MRNA FOR DIAGNOSIS AND TREATMENT OF NEUROLOGICAL PATHOLOGIES

This is a U.S. National Phase Application of PCT/US93/12161 filed under 35 U.S.C. 371 on Dec. 14, 1993 which is a continuation-in-part application of U.S. application Ser. No. 07/991,582 filed Dec. 14, 1992, now abandoned.

Pursuant to 35 U.S.C. §202(c), it is hereby acknowledged that the U.S. Government has certain rights in the invention described herein, which was made in part with funds from the National Institutes of Health, grant number USPHSMH 42148.

Pursuant to 35 U.S.C. §202(c), it is hereby acknowledged that the U.S. Government has certain rights in the invention described herein, which was made in part with funds from the National Institutes of Health.

FIELD OF THE INVENTION

This invention relates to treatment of pathological conditions associated with abnormalities in dopamine receptors. In particular, it relates to diagnosis and treatment of patients having such pathological conditions by administration of oligonucleotides antisense to one or more mRNA molecules encoding one of the several dopamine receptors.

BACKGROUND OF THE INVENTION

Abnormal activity of the dopaminergic nervous system has been implicated in a number of motor and behavioral disorders including Parkinson's disease, Huntington's disease, tardive dyskinesia, certain forms of schizophrenia and other dystonias and dyskinesias. Dysfunctions of the dopaminergic system may be caused either by a reduced or increased activity of the dopaminergic system or by the inability of the systems to be modulated by a changing external or internal environment.

Dopamine is one of the major catecholamine neurotransmitters in the mammalian brain. Dopamine exerts its effect in part by binding to G protein-coupled dopamine receptors. Pharmacological and molecular biological studies have shown that the dopamine receptor has at least five subtypes, designated $D_{1-5}$. The best characterized of these are $D_1$ and $D_2$. The $D_2$ subtype exists in a long and short form, the long form having a larger intracellular loop than the short form. These receptor subtypes appear to be anatomically, biochemically and behaviorally distinct. For example, $D_1$ and $D_2$ receptors have different anatomical distributions, in that only $D_1$ receptors are found in the retina and only $D_2$ receptors are found in the pituitary, but both $D_1$ and $D_2$ are found in the striatum and substantia nigra. $D_1$ and $D_2$ receptors are reported to have opposite biochemical effects on adenylate cyclase activity, and stimulation of $D_1$ and $D_2$ receptors produces different behavioral responses. See Weiss et al., Neurochemical Pharmacology—A Tribute to B. B. Brody, E. Costa, ed.; Raven Press, Ltd., New York; pp. 149–164 (1989).

Recently, three new subtypes of dopamine receptors have been discovered. On the basis of nucleotide and amino acid sequence homology, $D_3$ and $D_4$ have been found to be related to $D_2$, and $D_5$ is related to $D_1$. Hence, the dopamine receptor subtypes may be categorized into two subfamilies, $D_1$ and $D_5$ being members of the $D_1$ subfamily, and $D_2$, $D_3$ and $D_4$ being members of the $D_2$ subfamily. See Sibley et al., Trends in Pharmacological Sciences, 13: 61–69 (February, 1992).

The dopamine receptor subtypes can be separately and independently modulated through the administration of selective agonists and antagonists. For example, whereas dopamine and apomorphine are agonists of both $D_1$ and $D_2$ receptors, SKF 38393 (Setler et al., Eur. J. Pharmacol., 50: 419–30, 1978) is a selective agonist of only $D_1$ and quinpirole (Tsuruta et al., Nature, 292: 463–65, 1981) is a relatively selective agonist for the $D_2$ receptor. It should be emphasized, however, that the currently available dopaminergic drugs have only a relative selectivity for the various dopamine receptors. Indeed, there are recent reports suggesting that quinpirole may have a higher affinity for $D_3$ receptors than for $D_2$ receptors (see Sokoloff et al., Nature, 347: 146–151 (1990)).

It is not surprising, therefore, that the use of specific and nonspecific neuroleptic drugs in the treatment of dopaminergic disorders is contraindicated by the fact that such drugs often produce numerous side effects, presumably due to cross-reactivity with other dopamine receptor subtypes, or even with other classes of neuroreceptors. For example, the therapeutic action of many neuroleptic drugs appears to be due to a blockade of dopamine $D_2$ receptors. However, patients treated with such drugs often develop tardive dyskinesia, possibly because of the up-regulation of dopamine receptors. A further example is that benzazepines (such as SKF-38393), which are a major $D_1$ drug class, were recently found to be strongly cross-reactive with the serotonin 5-$HT_2$ receptor family. Nicklaus et al., J. of Pharmacol. Exp. Ther., 247: 343–48 (1988); Hoyer et al., Eur. J. Pharmacol., 150: 181–84 (1988). Additionally, clozapine is a favored antipsychotic in the treatment of socially withdrawn and treatment-resistant schizophrenics because it does not cause tardive dyskinesia. Clozapine has been found to preferentially bind the $D_4$ receptor with an affinity ten times higher than to the $D_2$ or $D_3$ receptors. Van Tol et al., Nature, 358: 149–152 (1992). However, clozapine treatment results in other side effects that are likely to be related to nonselectivity of the drug.

From the foregoing discussion, it can be seen that a need exists for improved selectivity in dopamine receptor drug classes. However, it is difficult to achieve such selectivity with classical pharmaceutical agents because the available drugs likely act on multiple neurotransmitter receptors and because the modulatory responsiveness of the nervous system to such compounds is not well understood. Therefore, it is difficult to separate the effect of drug cross-reactivity from a natural compensatory response of the nervous system to modulation of a specific receptor.

Molecular biological techniques provide a useful means to develop highly specific receptor modulatory agents. In the case of dopamine receptors, all five subtypes have been cloned from at least one biological source. Sequence information is available for all five subtypes. The availability of such information enables development of receptor-regulatory agents targeted to pre-translational stages of receptor expression. In particular, knowledge of the nucleotide sequence of dopamine receptor genes and messenger RNAs enables the selection and synthesis of antisense molecules capable of binding to critical targets on dopamine receptor mRNAs, thereby inhibiting or modifying translation.

The use of synthetic antisense oligonucleotides for therapeutic purposes was first proposed in 1978 and has been successfully accomplished in vitro and within cultured cells. See Uhlmann et al., Chemical Review, 90: 544–584 (1990). However, successful application of antisense therapy in vivo has been extremely limited. The delivery of antisense oligonucleotides to target cells in vivo is but one obstacle to overcome in developing successful antisense therapeutic agents. Even if biologically significant amounts of antisense molecules reach target cells and bind to selected target sites on mRNA, a subsequent effect on regulation of translation is not guaranteed. Regulation of protein synthesis is highly dependent upon the number of messenger RNA molecules present in the cell that encode a particular protein, as well as the rate of protein synthesis. Furthermore, even if expression of a selected protein can be modulated by an antisense molecule, whether such modulation would have an effect on the associated pathological condition cannot be predicted.

There have been a few reports of successful modulation of various pathological conditions by antisense therapy in rodents. Oligonucleotides antisense to the proto-oncogene c-myc have been administered in vivo to rats to suppress the intimal accumulation of rat carotid arterial smooth muscle cells (Simons et al., Nature 359: 67–70 (1992). Antisense oligonucleotides have also been used in viva in mice. An 18-nucleotide phosphorothioate oligodeoxynucleotide antisense to sequences encoding the interleukin I (IL-1) receptors, when injected subcutaneously into mice, markedly inhibited the infiltration of neutrophils in response to subsequent injections of IL-1. Burch and Mahan, J. Clin, Invest., 88: 1190–1196 (1991). In another study, repeated injection of antisense oligonucleotide (3×0.5 nmol per day) conferred 30–70% protection against a normally fatal infection of encephalitis in mice. See Uhlmann et al., supra at 577.

It can be surmised from the foregoing examples that antisense technology has great potential in in vivo therapy for the treatment of disease. However, this potential, to date, remains largely unexplored.

SUMMARY OF THE INVENTION

According to one aspect of the present invention, a method is provided for controlling the expression of a pre-determined dopamine receptor in a living organism. The method comprises providing an antisense oligonucleotide capable of binding specifically to an expression-controlling sequence of a nucleic acid encoding the dopamine receptor. The antisense oligonucleotide is administered to the living organism under conditions whereby the oligonucleotide enters cells expressing the dopamine receptor and binds specifically to the expression-controlling sequence of the nucleic acid encoding the dopamine receptor, in an amount sufficient to control the expression of the dopamine receptor.

According to another aspect of the present invention, a compound is provided that is useful for controlling expression of a pre-determined dopamine receptor in a living organism. The compound comprises an antisense oligonucleotide analog capable of entering a cell expressing such a dopamine receptor and binding specifically to an expression-controlling sequence of a nucleic acid that encodes the dopamine receptor, in an amount sufficient to control expression of the dopamine receptor.

According to another aspect of the present invention, a method is provided for treating a pathological condition related to an abnormality in a dopamine receptor. Examples of such abnormal pathological conditions are Huntington's Disease, tardive dyskinesia, various forms of schizophrenia, dementia, as well as abnormal vascular control, abnormal circadian rhythms and abnormal visual activity. The method comprises administering to a patient having such a pathological condition a pharmaceutical preparation comprising an antisense oligonucleotide analog capable of entering a cell expressing the dopamine receptor and binding specifically to a nucleic acid encoding the dopamine receptor, in an amount sufficient to affect the level of expression of the dopamine receptor, thereby alleviating the pathological condition.

According to another aspect of this invention, a pharmaceutical preparation is provided for treating a pathological condition related to a dopamine receptor abnormality. This pharmaceutical preparation comprises, in a biologically compatible medium, an antisense oligonucleotide capable of entering a cell expressing the dopamine receptor and binding specifically to a nucleic acid encoding the dopamine receptor, in an amount sufficient to affect the level of expression of the dopamine receptor.

In yet another aspect of the present invention, there is provided an antisense oligonucleotide analog for inhibiting $D_2$ dopamine receptor agonist-induced rotational behavior in mammals. When administered by intraventricular injection, such an antisense oligonucleotide analog is capable of crossing a biological membrane and binding specifically to a nucleotide sequence comprising a translation start site of mRNA encoding the $D_2$ dopamine receptor, in an amount sufficient to affect the level of expression of the $D_2$ receptor.

In another aspect of the present invention, there is provided an antisense oligonucleotide analog for inhibiting $D_1$ dopamine receptor agonist-induced grooming behavior and rotational behavior in mammals. When administered by intraventricular injection, such an antisense oligonucleotide analog is capable of crossing a biological membrane and binding specifically to a nucleotide sequence comprising a translation start site of mRNA encoding the $D_1$ dopamine receptor, in an amount sufficient to affect the level of expression of the $D_1$ receptor.

According to a further aspect of the present invention, methods are provided for diagnosing pathological conditions relating to a dopamine receptor abnormality. In one such method, a patient whose pathological condition is suspected of being related to a particular dopamine receptor abnormality is administered at least one antisense oligonucleotide capable of crossing a biological membrane and binding specifically to a nucleotide sequence encoding a pre-determined dopamine receptor subtype, in an amount sufficient to affect the level of expression of the particular subtype. It is then observed whether or not the pathological condition is alleviated as a result of administering the antisense oligonucleotides. Alleviation of the pathological condition is thus diagnostic of an abnormality in the pre-determined dopamine receptor subtype.

Another diagnostic method provides a way of determining if expression of a pre-determined dopamine receptor subtype in a living organism is related to a pre-determined pathological condition in that living organism. The method comprises first providing a living organism having the pathological condition, as well as providing an antisense oligonucleotide capable of binding specifically to an expression-controlling sequence of a nucleic acid that encodes the dopamine receptor subtype. The antisense oligonucleotide administered to the living organism under conditions whereby the antisense oligonucleotide enters cells expressing the dopamine receptor subtype and bind specifically to the expression-controlling sequence of the nucleic acid that encodes the dopamine receptor subtype, in an amount sufficient to control expression of the dopamine receptor subtype. It is then observed whether or not such control of expression of the dopamine receptor subtype alleviates the pathological condition. Alleviation of the pathological condition indicates that expression of the dopamine receptor subtype is related to the pathological condition in the living organism.

According to another aspect of the present invention, the compound is provided for controlling expression of a pre-determined dopamine receptor in cells expressing that receptor. The compound comprises an antisense oligonucleotide capable of entering the cell and binding specifically to an expression-controlling sequence of a nucleic acid that encodes the dopamine receptor, in an amount sufficient to control expression of the dopamine receptor.

According to still another aspect of the present invention, a method is provided for determining if a test compound is a specific agonist or antagonist of a pre-determined dopamine receptor subtype (the term "agonist or antagonist" is sometimes substituted herein by the general term "regulator"). According to the methods, cells expressing the pre-determined dopamine receptor subtype are provided; however, the cells may express more than one dopamine receptor subtype. The cells possess at least one detectable biological function that is related to a response of the pre-determined dopamine receptor subtype caused by the specific regulator. A quantity of the cells are pre-treated with an antisense oligonucleotide capable of entering the cells and binding specifically to an expression-controlling sequence of a nucleic acid that encodes the pre-determined dopamine receptor subtype, under conditions whereby the antisense oligonucleotides enters the cells and binds to the expression-controlling sequence in an amount sufficient to control expression of the specific dopamine receptor subtype. The pre-treated cells, and an equivalent quantity of non pre-treated cells, are exposed to the test compound under conditions promoting the specific regulatory effect, if any, of the test compound. Changes are then detected in the related biological function, if any have occurred, in the pre-treated and non pre-treated cells, to observe whether or not the control of expression of the specific dopamine receptor subtype by the antisense oligonucleotide alleviates the change in the related biological function (if any exists) exerted by the test compound. Any alleviation observed in the pre-treated cells as compared to the non pre-treated cells is indicative that the test compound is a specific regulator (agonist or antagonist) of the pre-determined dopamine receptor subtype. Thus, by observing the effect of a potential agonist or antagonist of a specific dopamine receptor subtype in the presence or absence of the antisense oligonucleotide specific for that receptor subtype, potentially useful dopamine regulating compounds may be screened for their specific agonistic or antagonistic effect on a particular dopamine receptor subtype.

In preferred embodiments of the present invention, the antisense oligonucleotide is an oligonucleotide analog having improved stability and membrane permeability as compared with an unmodified oligonucleotide. The antisense oligonucleotide analog is capable of crossing a biological membrane in order to enter cells and thereafter bind specifically with the selected nucleic acid sequence. The selected nucleic acid sequence preferably comprises a translation start site of mRNA encoding the dopamine receptor. The biologically compatible medium is preferably formulated to enhance the lipophilicity and membrane-permeability of the antisense oligonucleotide.

The methods and antisense compounds of the present invention provide notable advantages over currently available compounds and methods for treating abnormalities of the dopamine nervous system. Most notably, these methods and compounds provide improved selectivity in the treatment of abnormalities associated with a specific dopamine receptor subtype. Potent, highly specific antisense molecules may be designed, based on knowledge of the nucleotide sequences encoding the dopamine receptor subtypes. Target sequences may be selected which are specific to a pre-determined dopamine receptor subtype, yet critical to expression of the dopamine receptor (e.g., a translation start site). Because such antisense compounds have now been shown to be capable of entering dopaminergic cells and exerting an effect on a pathological condition associated with the dopamine receptor, such compounds and methods will be useful in numerous therapeutic and diagnostic applications relating to the dopaminergic nervous system.

BRIEF DESCRIPTION OF THE DRAWINGS

The present invention will be more fully appreciated and better understood when considered in conjunction with the accompanying drawings, wherein:

FIGS. 7A and 7B are a pair of graphs showing the effect of $D_2$ antisense oligonucleotides on $D_1$ and $D_2$ dopamine receptors in mouse striatum, wherein the graph on the left shows that binding of [$^3$H]raclopride, a specific ligand for $D_2$ receptors, is reduced in the lateral striatum by treatment with a $D_2$ antisense oligonucleotide, as compared with the medial striatum of lesioned brains or the lateral and medial striatum of unlesioned brains; the graph on the right shows that binding of [$^3$H]SCH 23390, a specific ligand for $D_1$ receptors, is not reduced in lateral or medial striatum of lesioned or unlesioned brain as a result of treatment with a $D_2$ antisense oligonucleotide.

DETAILED DESCRIPTION OF THE INVENTION

Figure 1:
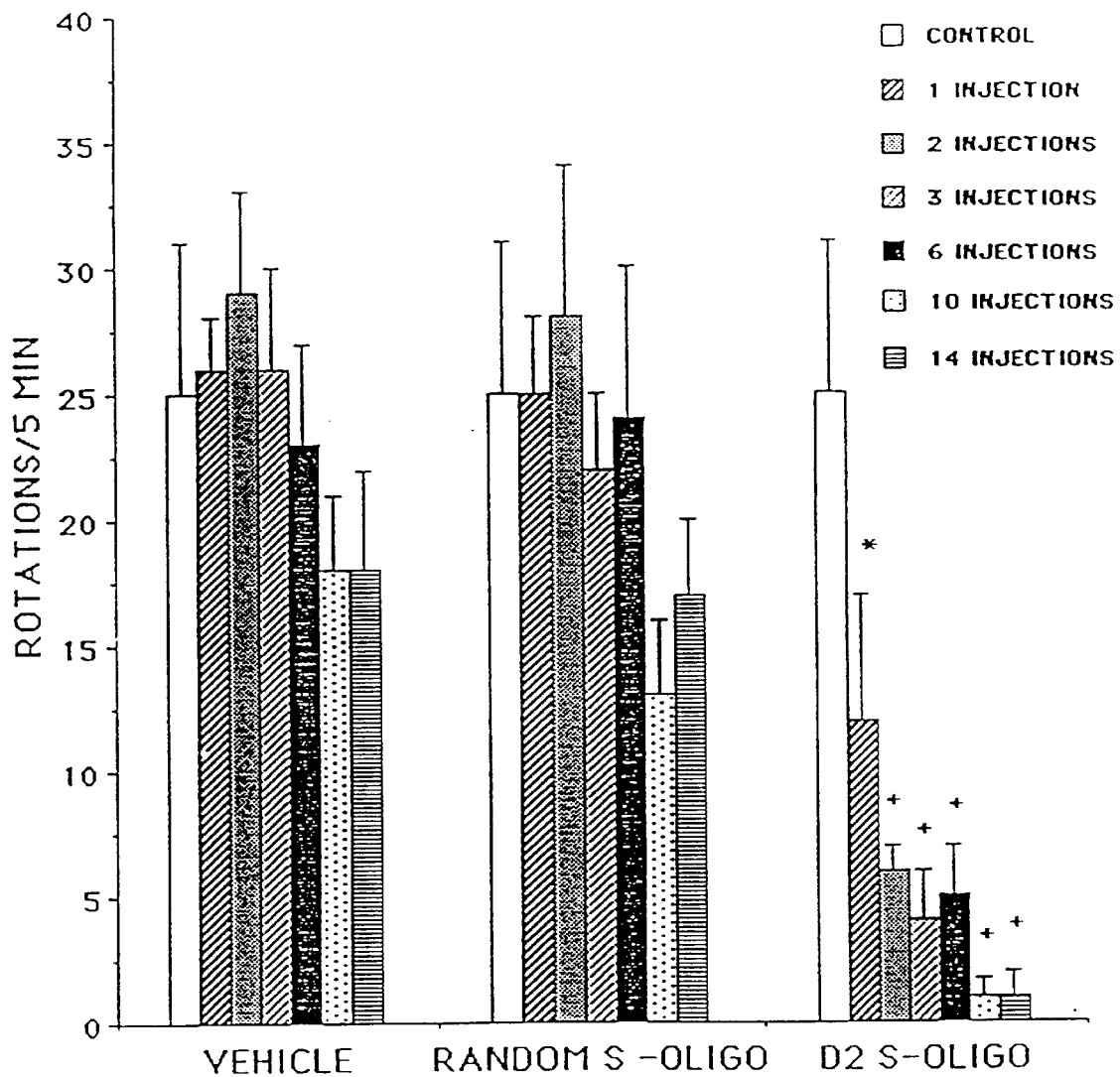
FIG. 1 is a graph showing the effect of repeated injections of a $D_2$ antisense oligonucleotide on quinpirole-induced rotational behavior in mice with unilateral 6-hydroxydopamine (6-OHDA) lesions.

In accordance with the present invention, it has now been discovered that an oligodeoxynucleotide antisense to $D_1$ or $D_2$ dopamine receptor mRNAs, when administered in vivo to mice, can inhibit specific $D_1$ or $D_2$ dopamine mediated behaviors.

The effect of the $D_2$ antisense oligonucleotide on $D_2$ receptor-mediated behaviors was demonstrated as follows. A 20-nucleotide phosphorothioate oligodeoxynucleotide ($D_2$ S-oligo) was constructed to be antisense to sequences of the mouse $D_2$ dopamine receptor mRNA, specifically of sequences encompassing the translation start site. As a control, an oligodeoxynucleotide with the same proportion of bases as in the $D_2$ S-oligo, but having a random sequence (random S-oligo) was similarly prepared. Mice with unilateral 6-hydroxydopamine (6-OHDA) lesions were intraventricularly or intrastriatally administered the $D_2$ S-oligo (2.5 nmol/2 μl) or the random S-oligo for varying periods of time. The mice were then challenged with the $D_2$ dopamine receptor agonist quinpirole and rotational behavior was measured.

The results showed that administering the $D_2$ S-oligo inhibited rotations induced by quinpirole and that the reduction in behavior was related to the amount and length of time the $D_2$ S-oligo was given. For example, mice treated with the $D_2$ S-oligo showed a significant reduction in quinpirole-induced rotational behavior as early as 2 days after the initiation of treatment. By contrast, administering the $D_2$ S-oligo in doses that blocked the effects of quinpirole failed to block the rotational behavior induced by the $D_1$ dopamine agonist SKF 38393 or cholinergic agonist oxotremorine. Mice treated with the random S-oligo evidenced a normal rotational response to quinpirole and to SKF 38393. It was also demonstrated that direct injection of a $D_2$ antisense oligonucleotide into a discrete region of the brain (i.e., corpus striatum) resulted in the specific inhibition of a behavior induced by a $D_2$ agonist whose known site of action is that particularly area of the brain.

In situ hybridization histochemical studies of $D_1$ and $D_2$ dopamine receptor mRNAs using radiolabelled oligonucleotide probes and receptor autoradiography of $D_1$ and $D_2$ dopamine receptors using selective radioligands showed that repeated treatment with the $D_2$ S-oligo resulted in a significant reduction in the level of $D_2$, but not $D_1$, dopamine receptor mRNA and a reduction in the level of expression of $D_2$, but not $D_1$, dopamine receptors in mouse striatum, specifically in the dorsolateral regions, where 6-OHDA lesioning produced the largest increase in $D_2$ receptors. These results indicate that in vivo administration of a selective $D_2$ S-oligo results in selective blockade of a specific $D_2$ mediated behavior and that this action is likely to be caused by a reduction in the levels of $D_2$ dopamine receptors.

A similar procedure was followed for demonstrating the effect of a $D_1$ antisense oligonucleotide on $D_1$ receptor-mediated behaviors. A 20-nucleotide phosphorothioate oligodeoxynucleotide ($D_1$ S-oligo) was constructed to be antisense to sequences encompassing the translation start site of the mouse $D_1$ dopamine receptor mRNA. An oligodeoxynucleotide 20-mer having a random sequence was prepared as a control. Mice with unilateral 6-OHDA lesions were intraventricularly administered the $D_1$ antisense oligonucleotide or the random oligonucleotide for varying periods of time, then the mice were challenged with the $D_1$ dopamine receptor agonist SKF-38393, and rotational behavior was measured.

The results again showed that administering the $D_1$ antisense oligonucleotide inhibited rotations induced by SKF-38393, in direct relationship to the amount and length of time that the $D_1$ antisense oligonucleotide was administered. The effect of the $D_1$ antisense oligonucleotide was specific, in that doses of the oligonucleotide that blocked the effects of SKF-38393 failed to block the rotational behavior introduced by the $D_2$ dopamine agonist quinpirole or the cholinergic agonist oxotremorine.

In another procedure, non-lesioned mice were intraventricularly administered the $D_1$ antisense oligonucleotide or the random oligonucleotide for varying periods of time. The mice were then challenged with the $D_1$ dopamine receptor agonist SKF-38393, and agonist-induced grooming behavior was measured. The SKF-38393-induced grooming behavior was inhibited by the $D_1$ antisense oligonucleotide, in direct relation to the amount and length of time the $D_1$ antisense oligonucleotide was administered. These results, as well as the results obtained from 6-OHDA-lesioned mice, demonstrate that in vivo administration of the selective $D_1$ antisense oligonucleotide results in selective blockade of two specific $D_1$-mediated behaviors and that this action is also likely to be caused by a reduction in $D_1$ dopamine receptors.

The detailed description set forth below describes preferred methods for practicing the present invention. Methods for selecting and preparing antisense oligonucleotides are described, as well as methods for administering the antisense oligonucleotides in vivo. Specific in vitro and in vivo diagnostic and therapeutic applications of the oligonucleotides antisense to dopamine receptor mRNAs are also set forth.

I. Selection and Preparation of Antisense Oligonucleotides

Antisense oligonucleotides targeted to any known nucleotide sequence can be prepared by oligonucleotide synthesis according to known methods. Synthesis of oligonucleotides via phosphoramidite chemistry is preferred, since it is an efficient method for preparing oligodeoxynucleotide, as well as being adapted to many commercial oligonucleotide synthesizers.

Selection of a suitable antisense sequence depends on knowledge of the nucleotide sequence of the target mRNA, or gene from which the mRNA is transcribed. Although targeting to mRNA is preferred and exemplified in the description below, it will be appreciated by those skilled in the art that other forms of nucleic acid, such as pre-mRNA or genomic DNA, may also be targeted. Nucleotide sequence information is available for each of the five known dopamine receptor subtypes: (1) mouse $D_2$ (Mack et al., J. Neurochem., 57: 795–801, 1991) and human $D_2$ (Grandy et al., Proc. Natl. Acad. Sci. USA, 86: 9762–66, 1989); (2) rat $D_3$ (Sokoloff et al., Nature, 347: 146–151, 1990); (3) human $D_4$ (Van Tol et al., Nature, 350: 610–614, 1991); (4) rat $D_1$ (Zhou et al., Nature, 347: 56–80, 1990); and (5) human $D_5$ (Sunahara et al., Nature, 350: 614–619, 1991).

For maximum selectively, target sequences on dopamine receptor mRNAs of a selected subtype should be non-homologous to corresponding regions of mRNAs encoding other subtypes. For example, oligonucleotides antisense to regions encoding dopamine receptor transmembrane domains may not be suitable because of the high conservation of nucleotide sequences in those regions. Antisense oligonucleotides would be likely to bind to mRNAs encoding more than one subtype of dopamine receptor if such a target were chosen. See Van Tol et al., supra at 611.

Antisense oligonucleotides should, however, be targeted to regions of the selected mRNA that encompass sequences critical for expression of the receptor protein. Such sequences would include, but are not limited to, translation start sites or other known ribosome binding sites on a mature mRNA. Additionally, splice sites and/or polyadenylation signals of a pre-mRNA will provide suitable targets, as well as transcriptional start sites on DNA encoding dopamine receptor mRNA molecules. See Uhlmann et al., supra at 570.

In a preferred embodiment, the translation start site of a mature mRNA encoding a dopamine receptor subtype is selected as the target sequence.

Synthetic antisense oligonucleotides should be of sufficient length to hybridize to the target nucleotide sequence and exert the desired effect, e.g., blocking translation of an mRNA molecule. However, it should be noted that smaller oligonucleotides are likely to be more efficiently taken up by cells in vivo, such that a greater number of antisense oligonucleotides may be delivered to the location of the target mRNA. Preferably, antisense oligonucleotides should be at least 15 nucleotides long, to achieve adequate specificity. In a preferred embodiment, a 20-nucleotide antisense molecule is utilized. In one preferred embodiment, this oligonucleotide encompasses the translation start site of mRNA encoding the mouse $D_2$ receptor. The nucleotide sequence is set forth below as sequence ID No. 1:

5'-GTGGATCCATTGGGGCAGTG-3'

In another preferred embodiment, the oligonucleotide encompasses the translation start site of mRNA encoding the mouse $D_1$ receptor. The nucleotide sequence is set forth below as Sequence ID No. 2.

5'-GTTAGGAGCCATCTTCCAGA-3'

In alternative preferred embodiments, antisense sequences encompassing the translation initiation codons of mRNAs encoding the human $D_1$, $D_2$, $D_4$ and $D_5$ dopamine receptors, may be utilized to inhibit expression of those receptors in vivo. Additionally, the antisense sequence for the $D_3$ dopamine receptor mRNA translation start site for rat may also be utilized. Examples of such antisense sequences are shown in Table 1 below.

Antisense oligonucleotide sequences of different lengths than those shown in Table 1 may also be utilized to advantage in the present invention. Also, antisense oligonucleotides may be targeted to other sites on RNA, and even DNA encoding the various dopamine receptors, as discussed earlier. Examples of antisense molecules targeted to the splice sites of dopamine receptor pre-mRNAs are also listed in Table 1 below.

TABLE 1

Oligonucleotides Antisense to Selected
Target Sites of Dopamine Receptor mRNAs and Pre-mRNAs

| Receptor Subtype | Antisense Oligonucleotide Sequence | Reference |
| --- | --- | --- |
| Human $D_1$ start codon | 5'-GAGTCCTCATCTTCCTAAGA-3' (Sequence ID No. 3) | Dearry et al., Nature, 347: 72–76 (1990) |
| Human $D_2$ start codon | 5'-GTGGATCCATCAGGGCGGTG-3' (Sequence ID No. 4) | Grandy et al. Proc. Natl. Acad. Sci. USA, 86: 9762–66 (1989) |
| Human $D_3$ start codon | 5'-CTCAGAGATGCCATAGCCCA-3' | Giros et al., C.R. Acad. Sci., 3: 501–08 (1990) |
| Rat $D_3$ start codon | 5'-GAGGTGCCATGGCCCACACA-3' (Sequence ID No. 6) | Sokoloff et al., Nature, 347: 147–151 (1990) |
| Human $D_4$ start codon | 5'-GGTTCCCCATGGCGCGCCCG-3' (Sequence ID No. 7) | Van Tol et al., Nature, 350: 610– |

TABLE 1-continued

Oligonucleotides Antisense to Selected
Target Sites of Dopamine Receptor mRNAs and Pre-mRNAs

| Receptor Subtype | Antisense Oligonucleotide Sequence | Reference |
|---|---|---|
| Human $D_5$ start codon | 5'-GCGGCAGCATTTCGGGCTGG-3' (Sequence ID No. 8) | Sunahara et al., Nature, 350: 614–619 (1991) |
| Human $D_1$ splice site | 5'-CTCCAAACGCCTTAAAAAGC-3' (Sequence ID No. 9) | Minowa et al., Proc. Natl. Acad. Sci. USA, 89: 3045–49 (1992) |
| Human $D_2$ splice site | 5'-CACCTACCTCCATCTCCAGC-3' (Sequence ID No. 10) | Grandy et al., Proc. Natl. Acad. Sci. USA, 66: 9762–66 (1969) |
| Human $D_4$ splice site | 5'-CGCGGCTCACCTCGGAGTAG-3' (Secuence ID No. 11) | Van Tol et al., Nature, 350: 610–614 (1991) |

Small oligonucleotides such as those described above are highly susceptible to degradation by assorted nucleases. Moreover, such molecules are may be unable to enter cells because of insufficient membrane permeability. For these reasons, practitioners skilled in the art generally synthesize oligonucleotides that are modified in various ways to increase stability and membrane permeability. The use of modified antisense oligonucleotides is preferred in the present invention. The term "antisense oligonucleotide analog" refers to such modified oligonucleotides, as discussed hereinbelow.

Several methods of modifying oligodeoxyribonucleotides are known in the art. For example, methylphosphonate oligonucleotide analogs may be synthesized wherein the negative charge on the inter-nucleotide phosphate bridge is eliminated by replacing the negatively charged phosphate oxygen with a methyl group. See Uhlmann et al., supra at 546–48. Another common modification, which is utilized in a preferred embodiment of the present invention, is the synthesis of oligodeoxyribonucleotide phosphorothioates. In these analogs, one of the phosphate oxygen atoms not involved in the phosphate bridge is replaced by a sulphur atom, resulting in the negative charge being distributed asymmetrically and located mainly on the sulphur atoms. When compared to unmodified oligonucleotides, oligonucleotide phosphorothioates are improved with respect to stability to nucleases, retention of solubility in water and stability to base-catalyzed hydrolysis. See Uhlmann et al., supra at 548–50; Cohen, J. S. (ed.) *Oligodeoxynucleotide: Antisense Inhibitors of Gene Expression*, CRC Press, Inc., Boca Raton, Fla. (1989).

Other modifications of oligodeoxyribonucleotides to produce stable, membrane permeable oligonucleotide analogs are commonly known in the art. For a review of such methods, see generally, Uhlmann et al., supra, and Cohen, supra which also describe methods for synthesis of such molecules. In addition, modified oligoribonucleotides may be utilized in the present invention. However, oligodeoxyribonucleotides are preferred due to their enhanced stability, ease of manufacture and the variety of methods available for analog synthesis.

Still other modifications of the oligonucleotides may include coupling sequences that code for RNase H to the antisense oligonucleotide. This enzyme (RNase H) will then hydrolyze the hybrid formed by the oligonucleotide and the specific targeted mRNA. Alkylating derivatives of oligonucleotides and derivatives containing lipophilic groups can also be used. Alkylating derivatives form covalent bonds with the mRNA, thereby inhibiting their ability to translate proteins. Lipophilic derivatives of oligonucleotides will increase their membrane permeability, thus enhancing penetration into tissue. Besides targeting the mRNAs, other antisense molecules can target the DNA, forming triple DNA helixes (DNA triplexes). Another strategy is to administer sense DNA strands which will bind to specific regulator cis or trans active protein elements on the DNA molecule.

Deoxynucleotide dithioates (phosphorodithioate DNA) may also be utilized in this invention. These compounds which have nucleoside-$OPS_2O$ nucleoside linkages, are phosphorus achiral, anionic and are similar to natural DNA. They form duplexes with unmodified complementary DNA. They also activate RNase H and are resistant to nucleases, making them potentially useful as therapeutic agents. One such compound has been shown to inhibit HIV-1 reverse transcriptase (Caruthers et al., INSERM/NIH Conference on Antisense Oligonucleotides and Ribonuclease H, Arcachon, France 1992).

II. Administration of Antisense Oligonucleotides

Antisense oligonucleotides as described herein are generally administered to a patient as a pharmaceutical preparation. The term "patient" as used herein refers to human or animal subjects.

The pharmaceutical preparation comprising the antisense oligonucleotides of the invention are conveniently formulated for administration with a acceptable medium such as water, buffered saline, ethanol, polyol (for example, glycerol, propylene glycol, liquid polyethylene glycol and the like), dimethyl sulfoxide (DMSO), oils, detergents, suspending agents or suitable mixtures thereof. The concentration of antisense oligonucleotides in the chosen medium will depend on the hydrophobic or hydrophilic nature of the medium, as well as the length and other properties of the antisense molecule. Solubility limits may be easily determined by one skilled in the art.

As used herein, "biologically acceptable medium" includes any and all solvents, dispersion media and the like which may be appropriate for the desired route of administration of the pharmaceutical preparation, as exemplified in the preceding paragraph. The use of such media for pharmaceutically active substances is known in the art. Except insofar as any conventional media or agent is incompatible with the antisense molecules to be administered, its use in the pharmaceutical preparation is contemplated.

Selection of a suitable pharmaceutical preparation depends upon the method of administration chosen. For example, antisense oligonucleotides may be administered by direct injection into the region of the brain containing dopaminergic neurons. In this instance, a pharmaceutical preparation comprises the antisense molecule dispersed in a medium that is compatible with cerebrospinal fluid. In a preferred embodiment, artificial cerebrospinal fluid (148 mM NaCl, 2.9 mM KCl, 1.6 mM $MgCl_2$ $6H_2O$, 1.7 mM $CaCl_2$, 2.2 mM dextrose) is utilized, and oligonucleotides antisense to the $D_1$ or $D_2$ receptor are provided directly to dopaminergic neurons by intraventricular injection. In another preferred embodiment, antisense oligonucleotide are administered by direct injection into the corpus striatum.

Oligonucleotides antisense to dopamine receptor mRNAs may also be administered parenterally by intravenous injection into the blood stream, or by subcutaneous, intramuscular or intraperitoneal injection. Pharmaceutical preparations for parenteral injection are commonly known in the art. If parenteral injection is selected as a method for administering the antisense oligonucleotides, steps must be taken to ensure that sufficient amounts of the molecules reach their target cells to exert a biological effect. The lipophilicity of the antisense molecules, or the pharmaceutical preparation in which they are delivered may have to be increased so that the molecules can cross the blood-brain barrier to arrive at their target locations. Furthermore, the antisense molecules may have to be delivered in a cell-targeted carrier so that sufficient numbers of molecules will reach the target cells. Methods for increasing the lipophilicity of a molecule are known in the art, and include the addition of lipophilic groups to the antisense oligonucleotides.

Phosphorothioate or methylphosphonate oligonucleotide analogs become widely dispersed in living tissues following intravenous injection. For example, experiments in mice, which provided a detailed analysis of the pharmacokinetics, biodistribution and stability of oligonucleotide phosphorothioates showed a widespread distribution of phosphorothioate-modified oligodeoxynucleotide in most tissues for up to 48 hours. Significant amounts were found in brain following intraperitoneal or intravenous administration. Agrawal et al., Proc. Natl. Acad. Sci. USA, 88: 7595–99 (1991). In another study, methylphosphonate oligonucleotides were injected into mouse tail veins and found to achieve a reasonably uniform distribution in mouse tissue. See Uhlmann et al., supra at 577, citing Miller et al., Anti-Cancer Drug Design, 2: 117 (1987).

Several techniques have been used to increase the stability, cellular uptake and biodistribution of oligonucleotides. Antisense oligonucleotides of the present invention may be encapsulated in a lipophilic, targeted carrier, such as a liposome. One technique is to use as a carrier for the oligonucleotide a liposomal preparation containing the cationic lipid N-[1-(2,3-dioleyloxy) propyl]-N,N,N-trimethyl ammonium chloride (D OT MA; lipofectin). This has been found to increase by about 1000 fold the potency of the antisense oligonucleotide ISIS 1570, which hybridizes to the AUG translation initiation codon of human intracellular adhesion molecule-1. Bennett et al., Mol Pharmacol., 41: 1023–1033 (1992). Phosphorothioates have been particularly useful for increasing the biodistribution and stability of oligodeoxynucleotide in mice as described above. Loading phosphorothioate oligonucleotides into liposomes, particularly pH sensitive liposomes, to increase their cellular uptake has also been used with some success. Loke et al., Curr. Topics Microbiol. Immunol., 141: 282–289 (1988); Connor and Huang, Cancer Res., 46: 3431–3435 (1986).

Additional means by which antisense oligonucleotides may be administered include oral or rectal administration into the gastrointestinal tract, as well as intranasal or opthalmic administration.

The pharmaceutical preparation is formulated in dosage unit form for ease of administration and uniformity of dosage. Dosage unit form, as used herein, refers to a physically discrete unit of the pharmaceutical preparation appropriate for the patient undergoing treatment. Each dosage should contain a quantity of active ingredient calculated to produce the desired effect in association with the selected pharmaceutical carrier. Procedures for determining the appropriate dosage unit are well known to those skilled in the art.

Figure 2:
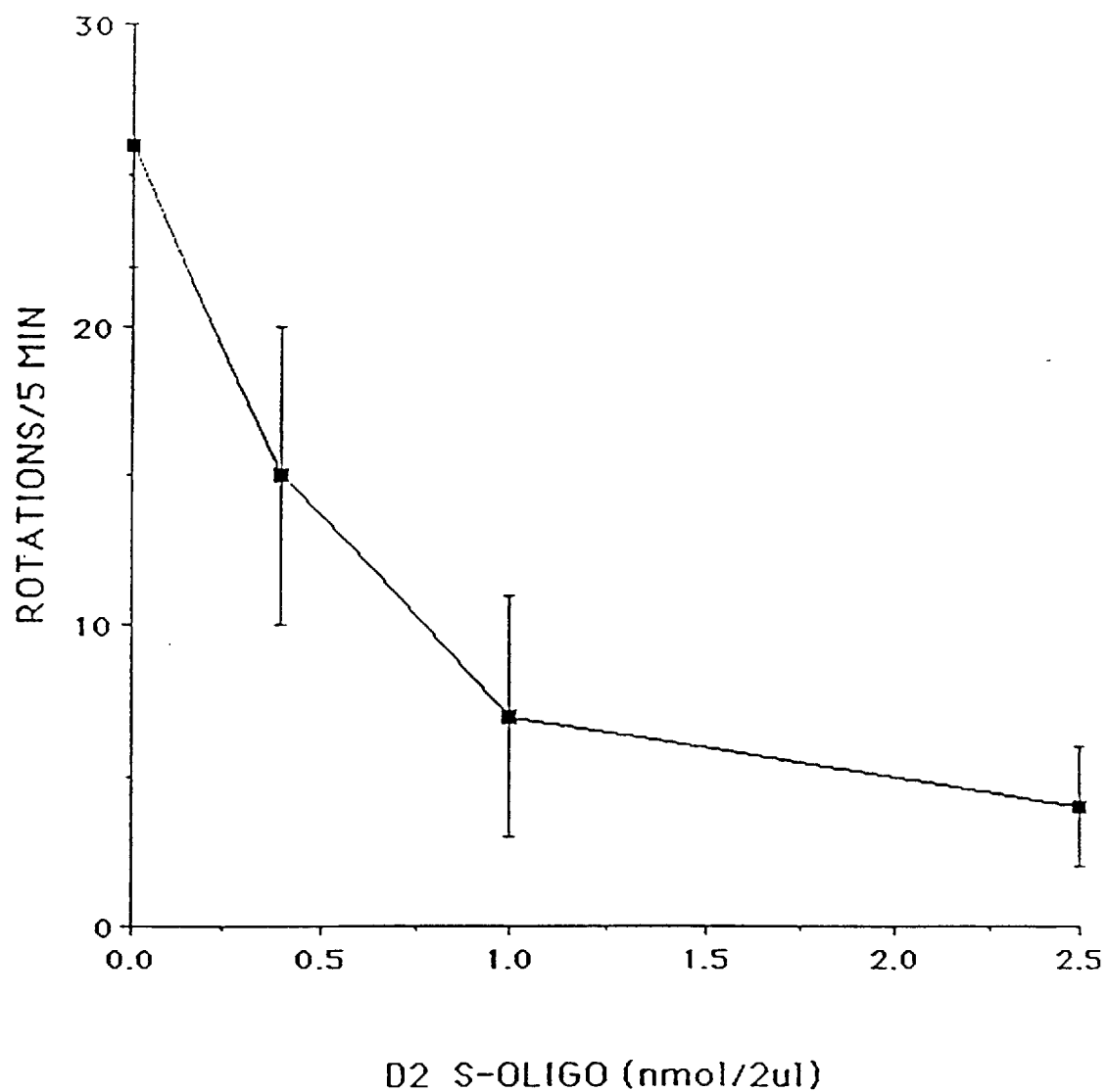
FIG. 2 is a graph showing the concentration-dependent inhibition of quinpirole-induced rotational behavior in mice with unilateral 6-OHDA lesions, resulting from administration of a $D_2$ antisense oligonucleotide.

A therapeutic effect of intraventricularly or intrastriatally injected oligonucleotides antisense to either $D_1$ or $D_2$ receptor mRNA has been observed in mice at a dosage unit concentration of 2.5 nmol/2 $\mu$l, for a mouse weighing about 20 g, or about 1.25 $\mu$mol/Kg body weight. Dosage units may be proportionately increased or decreased based on the weight of the patient. Appropriate concentrations for alleviation of a particular pathological condition may be determined by dosage concentration curve calculations, as known in the art and exemplified in Examples 1 and 2 and shown in FIGS. 2, 8 and 10.

The pharmaceutical preparation comprising the antisense oligonucleotides may be administered at appropriate intervals, for example, twice a day until the pathological symptoms are reduced or alleviated, after which the dosage may be reduced to a maintenance level. The appropriate interval in a particular case would normally depend on the condition of the patient.

III. Specific Applications

As described above, oligonucleotides antisense to dopamine receptor mRNA can be utilized therapeutically to alleviate pathological conditions related to expression of dopamine receptors. The therapeutic utility of such antisense molecules has been demonstrated in mice, as described more fully in the Examples. Antisense molecules can be specifically targeted to affect a selected dopamine receptor. This offers the distinct advantage over current therapeutic agents of being able to achieve a specific effect without side effects that result from cross-reaction with other receptors.

Because of their selectivity, antisense oligonucleotides may also be used in diagnosis of dopamine receptor-related pathological conditions. As a research diagnostic tool, specific antisense oligonucleotides may be utilized to correlate the expression of different receptor subtypes with the manifestation of physiological or biochemical effects. For example, antisense oligonucleotides directed at the different dopamine receptor mRNAs may be used as agents for screening potential dopamine receptor agonists and antagonists (sometimes referred to collectively herein as "dopamine receptor regulators"). It is well known that certain biochemical responses in dopaminergic cells and tissues are associated with stimulation of specific dopamine receptors. For instance, $D_1$ dopamine receptor agonists activate adenylate cyclase, thereby increasing the levels of cyclic AMP (cAMP) and increasing cAMP-mediated enzymatic activities, while $D_2$ dopamine receptor agonists decrease cAMP and cAMP-mediated enzymatic activities. $D_2$ agonists are known to cause a decrease in the release of acetylcholine from cholinergic cells. These biochemical events can be measured in vitro in dissected tissues, primary cultured cells or clonal cell lines, and are commonly used to measure the effect of a compound on a specific dopamine receptor, either instead of or along with the use of in vivo behavioral responses. Antisense oligonucleotides specific for mRNAs encoding the various dopamine receptors may be employed in such in vitro assays as follows (potential dopamine receptor agonists are exemplified): cells or tissues are treated in vitro with potential dopamine receptor agonists, and general agonists are identified. The cells or tissues are then treated with antisense oligonucleotides directed to the mRNAs of each specific dopamine receptor subtype, and the effect of the antisense oligonucleotides is observed in conjunction with the potential agonist being tested. If a specific antisense oligonucleotide suppresses the activity of the agonist, then it is likely that the agonist being tested is directed toward the specific dopamine receptor subtype to which the antisense oligonucleotide is directed.

Methods for measuring biochemical events triggered by dopamine receptor agonists and antagonists in vitro are well known in the art, and can be combined with antisense oligonucleotide treatments, using methods analogous to the in vivo methods described in Examples 1 and 2, and shown in FIGS. 4, 5, 9, 13, 15 and 16. Methods for measuring acetylcholine release in dissected tissues by prelabelling the tissues with [$^3$H]acetylcholine and then perfusing the tissues with the selected drugs are disclosed, e.g., by Tedford et al., Eur. J. Pharmacol., 211: 169–76 (1992) (measuring $D_1$ receptor antagonists), Drukarch et al., J. Neurochem., 52: 1680–85 (1991) (measuring $D_2$ agonist-induced decreases in in vitro release of acetylcholine) and Wang et al., Neuropharmacology, 32: 85–91 (1993) (measuring increase in release of acetylcholine induced by $D_1$ agonists in striatal slices). Increases or decreases in cAMP or cAMP-regulated enzymes may also be measured in dissected tissues, according to the method of, e.g., Lankford et al., Proc. Natl. Acad. Sci. USA, 85: 2839–43 (1988) (dissected chicken retinas), as well as in primary cell cultures, according to methods disclosed by, e.g., Chneiweiss et al., Eur. J. Pharmacol., 189: 287–92 (1990) (stimulation of $D_1$ receptors in primary cultures of striatal neurons). Clonal cell lines are also available for measuring biochemical responses to stimulation or suppression of various dopamine receptors. For example, several cell lines expressing substantially only $D_1$ or $D_2$ receptors on their surfaces have been disclosed by Monsma et al., Brain Res., 492: 314–24 (1989). Such cell lines may be used to advantage to screen potential agonists or antagonists of $D_1$ or $D_2$ dopamine receptors in conjunction with antisense oligonucleotides directed to $D_1$ or $D_2$ dopamine receptor mRNAs, in accordance with the present invention. As other dopamine-mediated biochemical events are uncovered, the antisense oligonucleotides directed toward the various dopamine receptor mRNAs can be used to determine which dopamine receptor subtype is responsible for that particular dopamine-mediated event.

Thus, specific oligonucleotides antisense to each of the dopamine receptor mRNAs may be used as tools for uncovering the biological function of the different dopamine receptor subtypes. The exact function of the $D_1$ and $D_2$ dopamine receptors is still poorly understood, and there is virtually no knowledge of the biological function of the newly discovered dopamine receptor subtypes, such as $D_3$, $D_4$ and $D_5$ subtypes. The in vitro and in vivo administration of selective oligonucleotides antisense to each of the mRNAs encoding the individual dopamine receptor mRNAs may aid in uncovering the different functions of the various dopamine receptor subtypes. This, in turn, may lead to additional, novel treatments for disorders which may be caused by abnormal amounts, synthesis or function of these receptor subtypes.

Oligonucleotides antisense to dopamine receptor mRNAs may also be utilized as a clinical diagnostic tool. For example, a patient exhibiting a pathological condition suspected of being related to one or more dopamine receptors may be subjected to treatment with a panel of antisense oligonucleotides specific for each of the receptor subtypes. Alleviation of the pathological condition by one or more of the specific antisense molecule may indicate a direct association between that dopamine receptor subtype and the pathological condition exhibited by the patient.

The above-described methods and antisense compounds provide many advantages over existing treatments for schizophrenia and other diseases and disorders particularly associated with increased dopaminergic activity. Classical antipsychotic drugs used in the treatment of schizophrenia (e.g., chlorpromazine and haloperidol) act by blocking the interaction of dopamine with one or more of the dopamine receptors. Long term treatment with these drugs, however, often causes a compensatory increase or up-regulation of these receptors. This up-regulation of dopamine receptors is thought to be responsible for the common and debilitating motor disturbance, tardive dyskinesia.

Oligonucleotides antisense to the $D_2$ dopamine receptor mRNA, for example, will produce the beneficial clinical actions of classical anti-psychotics because they will reduce the number of dopamine receptors by inhibiting their formation. Moreover, because antisense oligonucleotides reduce the number of dopamine receptors by inhibiting receptor synthesis, they are unlikely to produce the up-regulation of dopamine receptors that is produced by classical anti-psychotic agents. Therefore, it would be unlikely that they would induce tardive dyskinesia. Indeed, it is likely that these compounds will be useful in treating the tardive dyskinesia that classic anti-psychotics may have already produced in schizophrenic patients. Moreover, antisense oligonucleotides may even be useful as therapeutic agents in conjunction with classic anti-psychotic agents to prevent the formation of tardive dyskinesia.

The invention has the further advantage of producing selective changes in the dopamine receptor. As already stated, the classical anti-psychotic drugs produce relatively non-selective action on the various dopamine receptors. Moreover, they have an inhibitory effect on receptors for other neurotransmitters, including acetylcholine, norepinephrine, histamine and serotonin. This results in a number of other undesirable side effects, including dry mouth, blurred vision, constipation, orthostatic hypotension, hypothermia, urinary retention and endocrine disturbances. The ability to design selective antisense oligonucleotide that would not cause such side effects by inhibiting receptors of other neurotransmitters is a notable advantage of the present invention.

The following examples are provided to describe the invention in further detail. These examples are intended merely to illustrate and not to limit the invention.

EXAMPLE 1

Inhibition in 6-hydroxydopamine Lesioned Mice of Quinpirole-Induced Rotational Behavior by Administration of an Oligonucleotide Antisense to the $D_2$ dopamine Receptor mRNA Based on the sequence for the $D_2$ dopamine receptor mRNA, a 20-mer phosphorothioate oligodeoxy-nucleotide (referred to herein as $D_2$ antisense or $D_2$ S-oligo) antisense to a region surrounding the initiation codon (−10 to +10) of the mouse $D_2$ dopamine receptor mRNA, 5'-GTGGATCCATTGGGGCAGTG-3' (Sequence ID No. 1), was designed and synthesized. A 20-mer phosphorothioate oligodeoxynucleotide having a random sequence (referred to herein as random oligo or random S-oligo), 5'-GTGCTTGACGCGGATGGTGA-3' (Sequence ID No. 12), was used as a control.

Unmodified oligodeoxynucleotide probes were synthesized on a MilliGen/Biosearch Cyclone Plus DNA Synthesizer (Burlington, Mass.), using standard phosphoramidite protocols with oxidation by iodine (Beucage and Caruthers, Tetrahedron Lett., 22: 1859–64, 1981). For phosphorothiate oligodeoxynucleotide, the oxidation solution was replaced with a sulfurization solution (Beaucage reagent, 3H-1,2-benzodithiole-3-one-1,1-dioxide) (Iyer et al., J. Am. Chem. Soc., 112: 1253–54, 1990) purchased from Glen Research (Sterling, Va.). By using the sulfurization reagent, each and every "O" group of the phosphodiester bond can be substituted with a sulfur group. Oligodeoxynucleotide were purified by reverse phase HPLC methods, followed by desalting on a NAP-25 column (Pharmacia; Sweden). The purity of oligonucleotides was analyzed by gel electrophoresis in 20% acrylamide, 7M urea, 89 mM Tris-borate buffer, pH 7.0.

Quinpirole (LY 171555; trans-(-)-4,4a,5,6,7,8,8a,9-octahydro-5-propyl-1H (or 2H)-pyrazolo (3,4 g) quinoline dihydrochloride) and oxotremorine were obtained from Sigma Chemical Co., St. Louis, Mo. SKF 38393 (2,3,4,5,-tetrahydro-7,8-dihydroxy-1-phenyl-1H-3 benzazepine HCl) was from Research Biochemicals, Inc.

Male Swiss-Webster mice were unilaterally lesioned in the corpus striatum with 6-hydroxydopamine (6-OHDA, Sigma Chemical Co.) (100 nmol/2 $\mu$l). Ten days after lesioning, animals were screened for positive rotational responses to the $D_2$ dopamine agonist quinpirole (5 $\mu$mol/kg, s.c.), the $D_1$ dopamine agonist SKF 38393 (80 $\mu$mol/kg, s.c.) and the cholinergic muscarinic agonist oxotremorine (5 $\mu$mol/kg, s.c.). Mice were considered to exhibit a supersensitive response if they demonstrated at least ten rotations per five minutes in response to acute injections of the $D_2$ agonist quinpirole. Rotations were defined as 360° tight circular turns (turns with radii no greater than one body length) occurring in a direction contralateral from the side of the 6-OHDA lesion.

Twenty days after lesioning, mice were injected intraventricularly into the lateral ventricle with vehicle (artificial cerebrospinal fluid (CSF)), $D_2$ S-oligo (2.5 nmol/2 $\mu$l) or random S-oligo (2.5 nmol/2 $\mu$l) twice daily for varying periods of time. Rotational behavior induced by quinpirole, SKF 38393 and oxotremorine were measured during a 5-min period 10 hr after the final injection of either the vehicle, the $D_2$ S-oligo or random S-oligo.

For tissue preparation, animals were killed by decapitation 2 hr after the last injection of $D_2$ S-oligo, random S-oligo and vehicle. The brains were rapidly removed and immediately frozen on dry ice. Ten-micron sections were cut on a cryostat and thaw-mounted onto gelatin-coated slides for in situ hybridization studies. Twenty-micron sections were prepared in the same manner for use in receptor autoradiography studies. All sections were kept at –70° C. until used.

The methods used for $D_2$ and $D_1$ dopamine receptor autoradiography were modified from those described by Kohler and Radesater, Neurosci. Lett., 66: 85–90 (1986) for the $D_2$ dopamine receptor and Boyson et al., J. Neurosci., 6: 3177–88 (1986) for the $D_1$ dopamine receptor. Dried tissue sections were preincubated twice for 5 min in cold 50 mM Tris-HCl buffer (pH 7.4), containing 1 mM $MgCl_2$, 2 mM $CaCl_2$, 5 mM KCl and 120 mM NaCl. Specific $D_2$ dopamine receptor binding was defined as the binding of 2 nM [$^3$H]raclopride in the absence and presence of 2 $\mu$M sulpiride. Specific $D_1$ dopamine receptor binding was defined as the binding of 2 nM [$^3$H]SCH 23390 in the absence and presence of 2 $\mu$M SCH 23390. Incubations were performed in 50 mM Tris-HCl buffer for 60 min at 25° C. The tissue sections then were washed twice with cold Tris-HCl buffer and dried with a cool air stream. Sections were then exposed to tritium-sensitive Hyperfilm (Amersham) for either 30 days (for $D_2$ dopamine receptors) or 5 days (for $D_1$ dopamine receptors). The lateral and medial portions of the corpus striatum, as defined by Joyce, Exp. Neurol., 113: 261–76 (1991), were analyzed separately. The optical densities of the selected brain areas on the film were determined using a Drexel's Unix-based Microcomputer Analysis System (DUMAS) (Feingold et al., Exp. Biol. & Med., 11: 175–201, 1986). The resultant autoradiographs were quantified by converting optical density readings to fmol of ligand bound per mg protein tissue using tritium brain standards as described by Zhou et al., Neurochem. Internat., 22: 301–311 (1993). Two adjacent sections were used for each measurement.

In situ hybridization histochemistry was performed to detect dopamine receptor mRNA in brain slices by procedures described by Weiss et al., Neurochem. Int., 20: 495–585 (1992). Coronal sections of brain were cut out on a cryostat, and the sections were fixed and hybridized with [$^{35}$S]-labelled oligodeoxynucleotide dopamine receptor mRNA probes. The probe used to simultaneously detect the long and short forms of the $D_2$ mRNA ($D_{2(L+S)}$) was a 40-mer oligonucleotide designed to be complementary to nucleotide positions from –10 to +30, based on the cDNA sequence for the $D_2$ dopamine receptor (Mack et al., supra). The probe used to detect only the long form of the $D_2$ mRNA ($D_{2(L)}$) was a 39-mer oligodeoxynucleotide complementary to nucleotide positions from 766 to 804 (Weiss et al., supra). The $D_1$ mRNA probe was a 36-mer oligodeoxynucleotide complementary to nucleotide positions from 1255 to 1290 (Zhou et al., Nature, 347: 76–80, 1990). After hybridization, the sections were washed and placed in an X-ray cassette with Hyperfilm-$\beta$ max. After several days exposure at room temperature, the film was developed and quantitatively analyzed using a DUMAS imager analyzer. Optical density values were derived from a standard curve constructed using Kodak optical density standards (Kodak photographic step Table No. 3) after subtracting the film background. Lateral and medial portions of the striatum were analyzed separately, and two adjacent sections were used for each measurement.

Single statistical comparisons of the drug-treated group to its control were performed using a paired or unpaired independent student's t-test as appropriate. Comparisons of two groups were performed using a two-way analysis of variance.

In one such procedure, and mice with unilateral 6-OHDA lesions were administered from 1 to 14 intraventricular injections of vehicle (2 $\mu$l of artificial CSF), $D_2$ S-oligo (2.5 nmol/2 $\mu$l) or random S-oligo (2.5 nmol/2 $\mu$l). The injections were made twice daily for 6 days and then once daily for 2 days. Rotational behavior induced by challenge injections of quinpirole was determined 10 hr after each injection of vehicle or oligomer. Results are shown in FIG. 1, wherein each point represents the mean of 5 to 10 mice. Vertical brackets indicate the standard error. *=$p<0.05$ compared to vehicle-treated mice. +=$p<0.001$ compared to vehicle- or random S-oligo-treated mice. Referring to FIG. 1, the results show that near maximum inhibition of quinpirole-induced rotational responses was seen after 2 injections of the $D_2$ S-oligo and that inhibition remained fairly constant throughout the 6 days of treatment with the $D_2$ S-oligo. The random S-oligo failed to produce significant inhibition of quinpirole-induced rotations at any time point.

In a variation of the above procedure, mice with unilateral 6-OHDA lesions were administered intraventricular injections of various doses of the $D_2$ S-oligo every 12 hr for three injections. Rotational behavior induced by quinpirole (5 μmol/kg, s.c.) was measured during a 5 min period 10 hr after the third injection of the $D_2$ S-oligo. Results are presented in FIG. 2, wherein each point represents the mean value of 4 to 5 animals. Vertical brackets indicate the standard errors. The results show that the $D_2$ S-oligo produced a dose-related inhibition of the rotational response to quinpirole.

Figure 3:
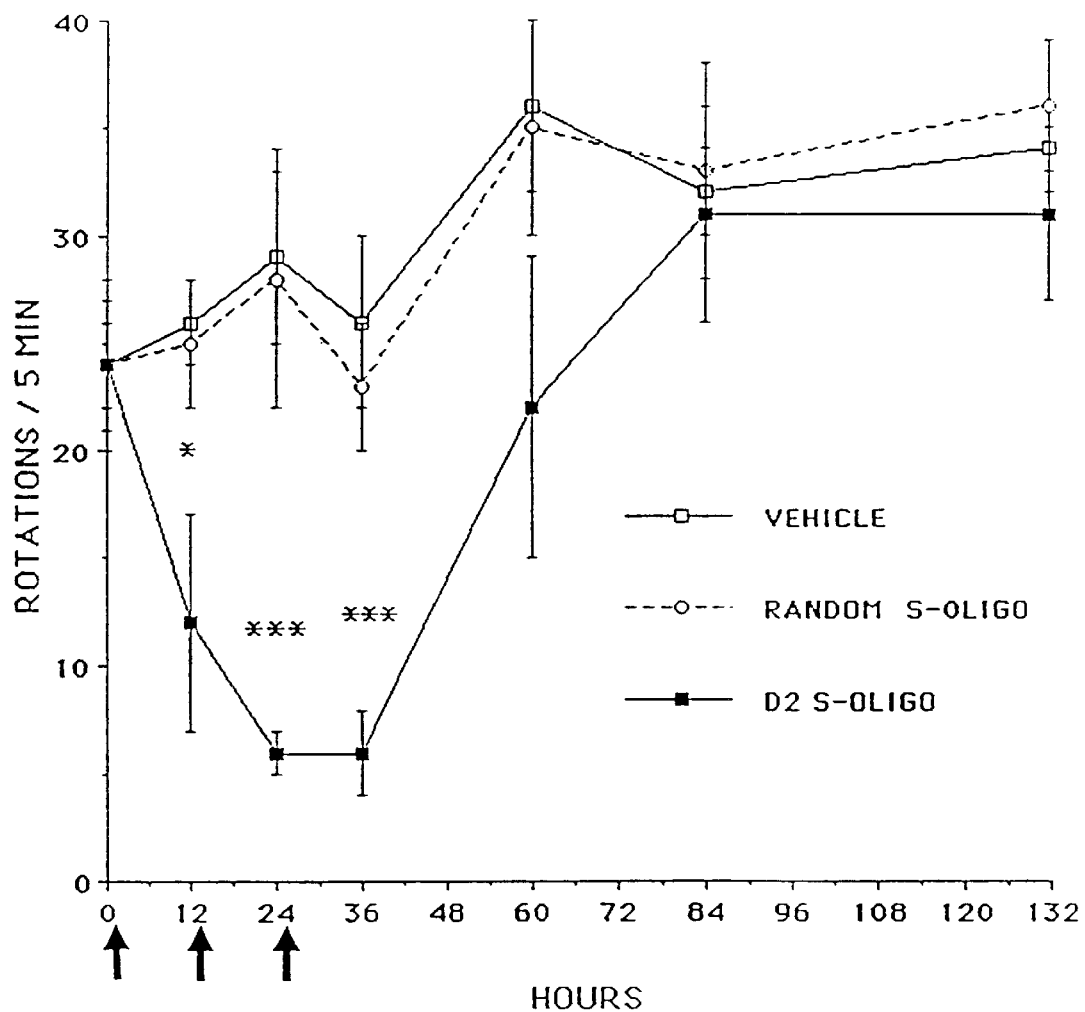
FIG. 3 is a graph showing the rate of recovery from $D_2$ antisense oligonucleotide inhibition of quinpirole-induced rotational behavior in unilaterally 6-OHDA-lesioned mice.

In another procedure, mice with unilateral 6-OHDA lesions were administered intraventricular injections of vehicle (2 μl of artificial CSF), $D_2$ S-oligo (2.5 nmol/2 μl) or random S-oligo (2.5 nmol/2 μl) three times at 10 hr intervals. Rotational behavior induced by quinpirole (5 μmol/kg, s.c.) was measured 12 hr after each injection of vehicle or oligomer. Mice were challenged with quinpirole again at 36, 60 and 108 hr after the last injection of vehicle or oligomer. Results are shown in FIG. 3, wherein each point represents the mean of 5 to 12 mice. Arrows indicate times at which injections were made. Vertical brackets indicate the standard error. $*=p<0.05$, $***=p<0.002$ compared to vehicle-treated or random S-oligo-treated mice. As can be seen from FIG. 3, the inhibitory effect of the $D_2$ S-oligo was statistically significant after the first injection, and was maximally effective after the second injection. The response to quinpirole recovered following cessation of the treatment with the $D_2$ antisense oligonucleotide and recovered completely within 48 hr. after the last injection of $D_2$ S-oligo.

Figure 4:
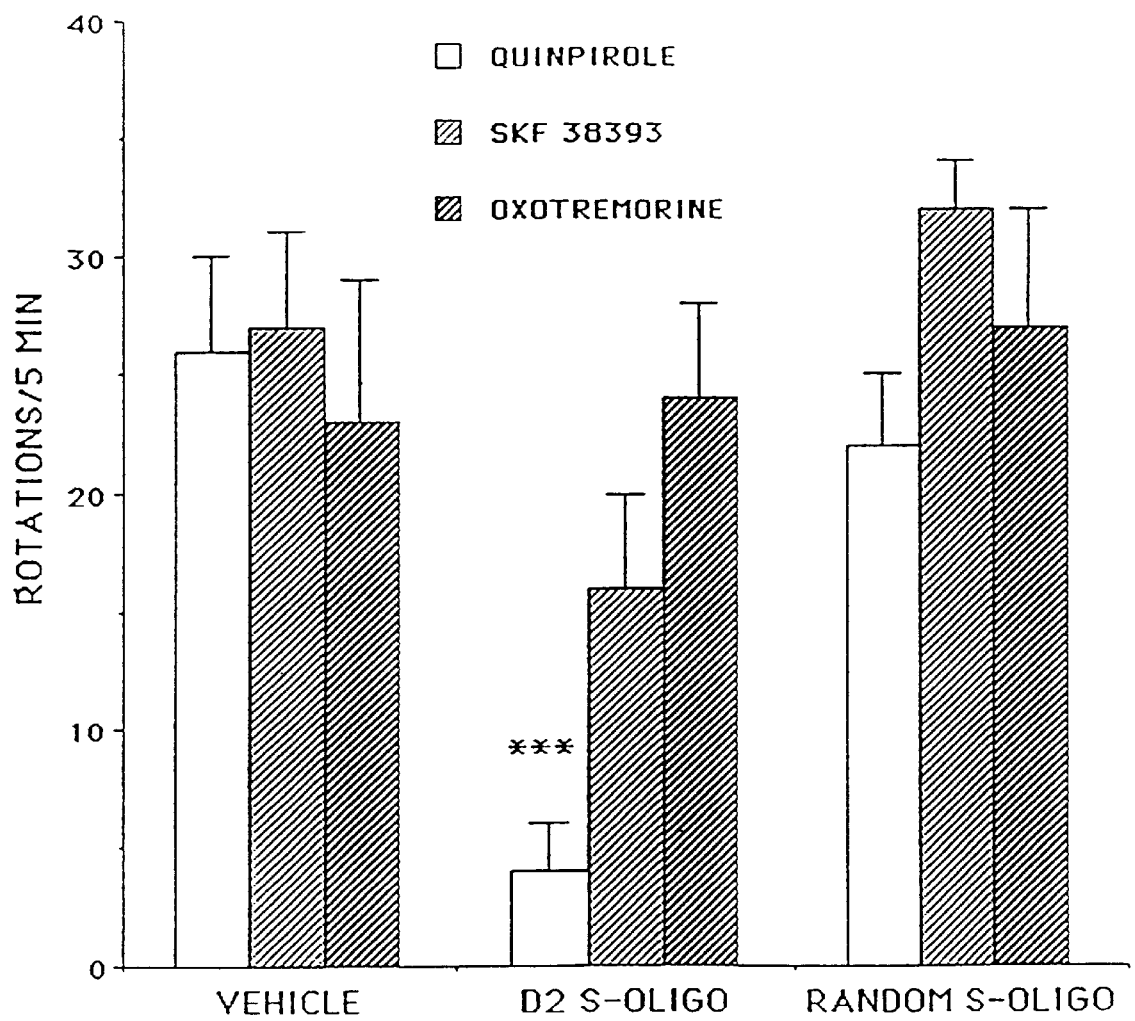
FIG. 4 is a graph showing the inhibition by $D_2$ antisense oligonucleotide, but not by an oligonucleotide of random sequence, of rotational behavior in unilaterally 6-OHDA-lesioned mice induced by quinpirole, and the absence of such inhibition when rotational behavior was induced by the $D_1$ agonist, SKF-38393, or the cholinergic agonist, oxotremorine.

In another procedure, mice with unilateral 6-OHDA lesions were administered intraventricular injections of vehicle (2 μl of artificial CSF), $D_2$ S-oligo (2.5 nmol/2 μl) or random S-oligo (2.5 nmol/2 μl) three times at 12 hr intervals. Rotational behavior induced by quinpirole (5 μmol/kg, s.c.,), SKF 38393 (80 μmol/kg, s.c.) and oxotremorine (5 μmol/kg, s.c.) was measured 10 hr after the last injection of vehicle or oligomer. Results are shown in FIG. 4, wherein each point represents the mean of 5 to 7 mice. Vertical brackets indicate the standard error. $***=p<0.001$ compared to vehicle- or random oligo-treated mice. Referring to FIG. 4, the results show that the $D_2$ S-oligo inhibited the rotational response to the $D_2$ agonist quinpirole but not that to the $D_1$ agonist SKF 38393 or to the muscarinic agonist oxotremorine.

Figure 5C:
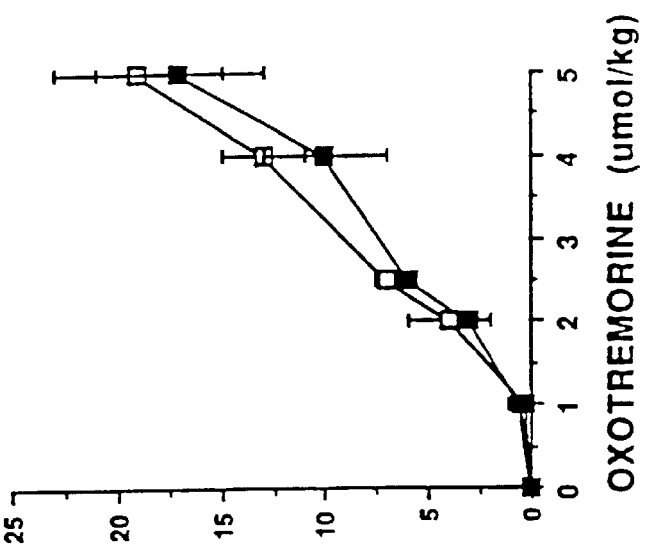
FIGS. 5A, 5B, and 5C are a set of graphs comparing the effect of $D_2$ antisense oligonucleotide administered to mice with unilateral 6-OHDA lesions to the corpus striatum on rotational behavior induced by varying doses of quinpirole (Graph A), SKF-38393 (Graph B) and is oxotremorine (Graph C).
Figure 5B:
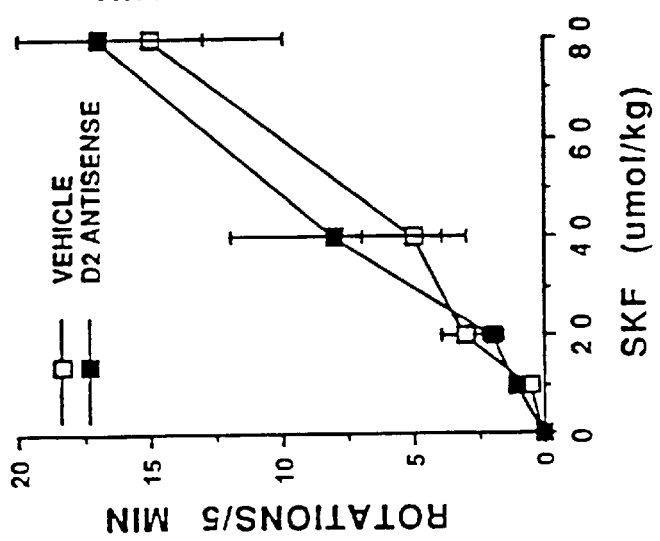
Figure 5A:
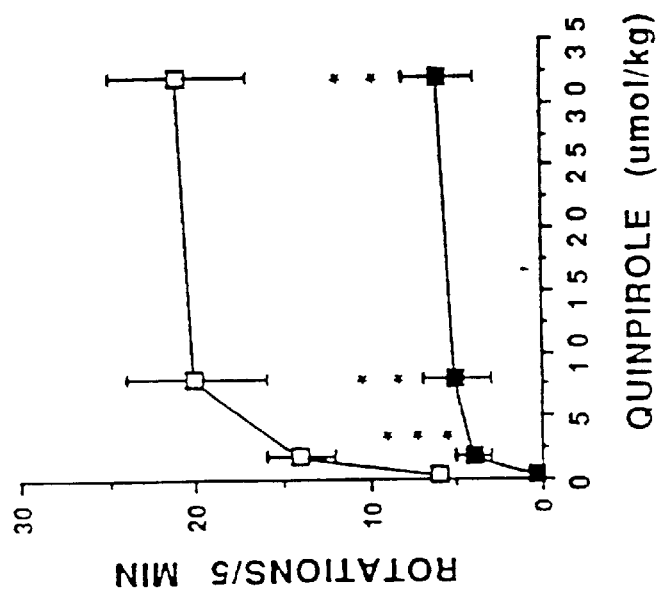

In a related procedure, mice with unilateral 6-OHDA lesions were administered intraventricular injections of $D_2$ S-oligo (2.5 nmol/2 μl) or vehicle (2 μl) with injections being made twice daily to two days and then once daily for two days. Mice were then challenged with varying doses of quinpirole, SKF-38393 or oxotremorine at 10 hours after the fourth (for quinpirole), fifth (for oxotremorine) or sixth (for SKF-38393) injection of vehicle or $D_2$ S-oligo. Results are shown in FIG. 5, wherein each point represents the mean value for 3–7 mice. Vertical brackets indicate the standard error. $=p<0.01$, $*=p<0.001$ compared to vehicle-treated mice. Referring to FIG. 5, the results show that treatment of mice with $D_2$ S-oligo significantly inhibits rotational behavior induced by quinpirole, when given at doses more than twenty times its $ED_{50}$ (FIG. 5A). By contrast, there was no significant inhibition of rotations induced by any dose of SKF-38393 (FIG. 5B) or oxotremorine (FIG. 5C). These experiments demonstrate the great selectivity by which the $D_2$-S-oligo inhibited $D_2$-mediated responses.

Figure 6:
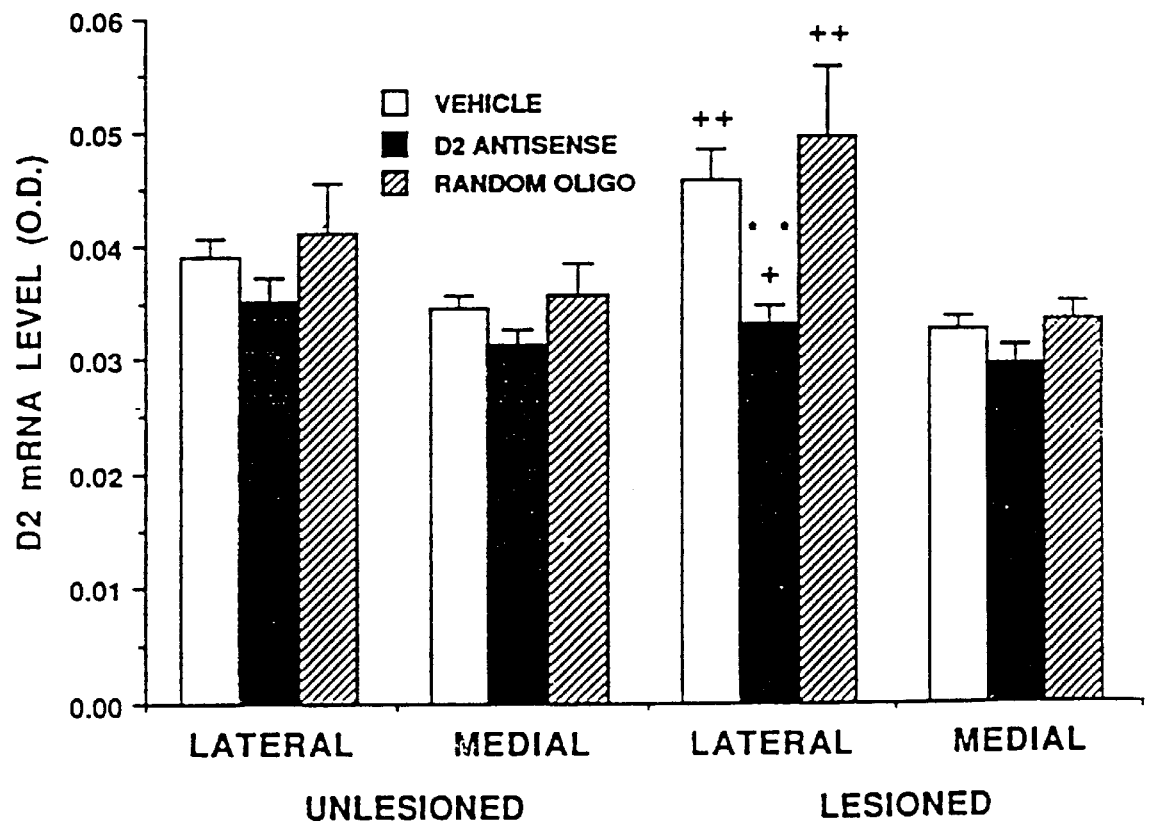
FIG. 6 is a graph showing that $D_2$ dopamine receptor mRNA in the lateral striatum is most greatly reduced by treatment with a $D_2$ antisense oligonucleotide, as compared with medial striatum of lesioned mouse brain and lateral or medial striatum of unlesioned mouse brain.

In another procedure, mice with unilateral 6-OHDA lesions were administered intraventricular injections of vehicle (2 μl of artificial CSF), $D_2$ S-oligo (2.5 nmol/2 μl) or random S-oligo (2.5 nmol/2 μl), twice daily for 6 days and then once daily for 3 days. Brains were removed 2 hr after the last injection of vehicle or oligomer and ten micron coronal sections at the level of the corpus striatum were prepared for in situ hybridization histochemistry, using a [$^{35}$S]-labelled $D_{2(L+S)}$ dopamine receptor mRNA oligodeoxynucleotide probe. Hybridization signals were detected by film autoradiography and analyzed using a DUMAS image analyzer. FIG. 6 shows a quantitative analysis of the in situ hybridization studies. Each bar represents the mean value from 4 mice. Vertical brackets indicate the standard error. $**=p<0.01$ compared to values from lesioned striata of vehicle-treated mice. $+=p<0.05$ compared to value from lesioned striata of random oligo-treated mice. $++=p<0.01$ compared to value from corresponding unlesioned striata.

As shown in FIG. 6, lesioning the striatum with 6-hydroxydopamine caused an increase in $D_{2(L+S)}$ dopamine receptor mRNA in corpus striatum; this increase was particularly evidence in the dorsolateral regions of the striatum. Lesioning produced statistically significant increases in the levels of $D_{2(L+S)}$ dopamine receptor mRNA in dorsolateral striatum of mice treated with vehicle or random oligo (FIG. 6A). No significant changes induced by lesioning were seen in medial striatum of any of the treatment groups. Treatment of mice with $D_2$ antisense decreased $D_{2(L+S)}$ dopamine receptor mRNA levels in striatum. These decreases were statistically significant in the dorsolateral, but not dorsomedial, region of the lesioned striatum when compared with that of the corresponding area of striatum of vehicle or random oligo-treated mice (FIG. 6A). No significant changes in the levels of $D_2$ dopamine receptor mRNA were seen in any region of striatum following treatment with the random oligo. In contrast to the effects of lesioning and $D_2$ antisense treatment on $D_2$ dopamine receptor mRNA levels, these treatments failed to significantly alter the levels of $D_1$ dopamine receptor mRNA in any area of striatum examined.

The results of the foregoing experiments utilized a $D_2$ mRNA probe that detects both the long and short forms of the $D_2$ mRNA transcripts ($D_{2(L+S)}$). To determine the effects of antisense treatment on just the long form of the $D_2$ mRNA, another probe, which detects only the long form of the $D_2$ mRNA ($D_{2(L)}$) was used. Mice with unilateral 6-hydroxydopamine lesions were administered intraventricular injections of either vehicle (2 μl of artificial CSF) or $D_2$ antisense (2.5 μmol/2 μl) twice daily for 6 days, and then once daily for 3 days. Brains were removed 2 hr after the 3rd, 7th and 15th injections of vehicle or $D_2$ antisense. Ten μm sections were prepared for in situ hybridization histochemistry using an [$^{35}$S]-labelled $D_{2(L)}$ dopamine receptor mRNA oligonucleotide probe. Hybridization signals were detected by film autoradiography and analyzed using a DUMAS image analyzer.

Table 2 shows the effects of $D_2$ antisense treatment on levels of $D_{2(L)}$ mRNA in mouse striatum, as determined by a quantitative analysis of autoradiographs generated following in situ hybridization histochemistry. Each value represents the mean ±SE of the number of experiments shown in parentheses. $*=p<0.05$, $**=p<0.01$ compared to values from corresponding lesioned striata of control, vehicle-treated mice.

TABLE 2

| | $D_{2(L)}$ mRNA LEVELS (PERCENT OF CONTROL VALUES) | | | |
|---|---|---|---|---|
| NUMBER OF | UNLESIONED | | LESIONED | |
| INJECTIONS | LATERAL | MEDIAL | LATERAL | MEDIAL |
| 3 | 96 ± 5 (5) | 92 ± 6 (5) | 87 ± 5 (%) | 99 ± 7 (5) |
| 7 | 85 ± 5 (3) | 88 ± 6 (3) | 80 ± 3* (3) | 83 ± 4 (3) |
| 15 | 86 ± 4 (4) | 97 ± 8 (4) | 74 ± 6** (4) | 94 ± 14 (4) |

The results shown in Table 2 were similar to those in which the $D_{2(L+S)}$ mRNA probe was used. Treatment with $D_2$ antisense significantly reduced the levels of $D_{2(L)}$ mRNA in dorsolateral, but not dorsomedial, striatum of 6-hydroxydopamine lesioned mice. No statistically significant effects of $D_2$ antisense treatment were seen in the unlesioned striatum. Table 1 shows further that the degree of which $D_{2(L)}$ mRNA levels decreased was related to the number of injections of $D_2$ antisense. Statistically significant decreases in $D_{2(L)}$ mRNA was found in dorsolateral striatum after 7 and 15 injections of $D_2$ antisense.

Yet another procedure was conducted to determine whether the $D_2$ antisense-induced reduction in the levels of $D_2$ dopamine receptor mRNA found in the dorsolateral striatum was associated with concomitant changes in the levels of $D_2$ dopamine receptors. Brains of mice treated with the $D_2$ antisense were analyzed for $D_1$ and $D_2$ dopamine receptors. Mice with unilateral 6-hydroxydopamine lesions were administered intraventricular injections of vehicle (2 μl of artificial CSF), $D_2$ antisense (2.5 nmol/2 μl) or random oligo (2.5 nmol/2 μl) twice daily for 6 days and then once daily for 3 days. Brains were removed 2 hr after the last injection of vehicle or oligomer, and 20 μm coronal sections were incubated with [$^3$H]raclopride (for $D_2$ receptors) or [$^3$H]SCH 23390 (for $D_1$ receptors), and the slides were processed for receptor autoradiography. The optical densities of the dorsolateral and dorsomedial areas of the striatum were analyzed separately using a DUMAS image analyzer. Results are shown in FIG. 7, wherein each bar represents the mean value from four mice. Vertical brackets indicate the standard error. *=p<0.05 compared to values from lesioned striata of vehicle or random oligo-treated mice. +=p<0.05 compared to values from corresponding unlesioned striata.

As shown in FIG. 7, lesioning in vehicle-treated or random oligo-treated mice increased the density of $D_2$ dopamine receptors (as assessed by the binding of [$^3$H] raclopride) in dorsolateral, but not dorsomedial, striatum (FIG. 7A). This increase was statistically significant in mice treated with the random oligo; the increase in vehicle-treated mice just failed to achieve statistical significance. Moreover, and in agreement with the results of similar experiments in which $D_2$ mRNA was studied, repeated administration of the $D_2$ antisense inhibited the increased density of $D_2$ dopamine receptors induced by 6-hydroxydopamine lesions in dorsolateral striatum (FIG. 7A). By contrast, the levels of $D_1$ receptors, assessed from the binding of [$^3$H]SCH 23390, in dorsolateral striatum of 6-hydroxydopamine lesioned mice was significantly lower than that in the unlesioned mice. As in the experiments in which $D_2$ dopamine receptor mRNA was studied, neither $D_2$ antisense nor random oligo significantly altered the levels of $D_1$ dopamine receptors in either lateral or medial striatum (FIG. 7B).

Figure 8:
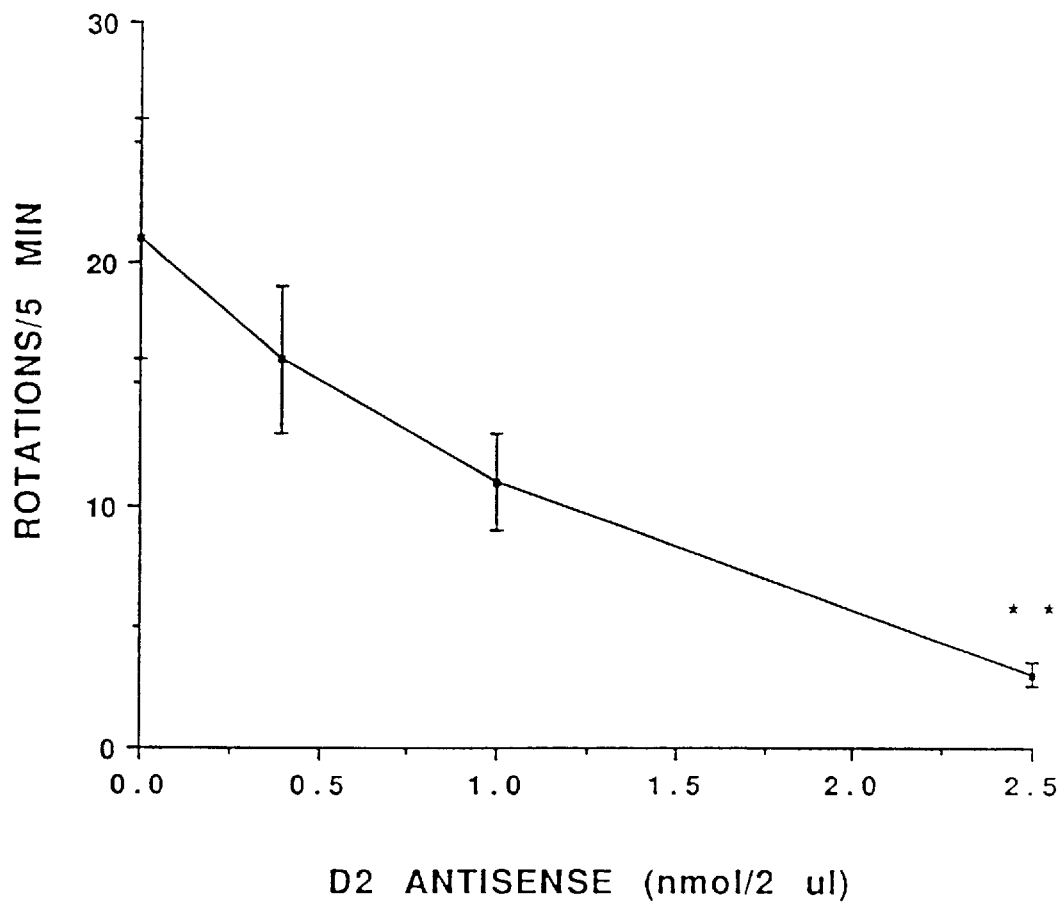
FIG. 8 is a graph showing the concentration-dependent inhibition of quinpirole-induced rotational behavior in mice with unilateral 6-OHDA lesions, resulting from direct intrastriatal of a $D_2$ antisense oligonucleotide.

The effect of direct intrastriatal administration of $D_2$ antisense oligonucleotides on quinpirole-induced rotational behavior was also tested. Mice with unilateral intrastriatal lesions induced by 6-OHDA were administered injections of various doses of the $D_2$ antisense oligonucleotide directly into one corpus striatum every 12 hr for four injections. Rotational behavior induced by acute injections of the $D_2$ dopamine receptor agonist quinpirole (5 μmol/kg, s.c.) was measured 10 hr after the last injection of $D_2$ S-oligo. Results are shown in FIG. 8. Each point represents the mean value from 4 mice. Vertical brackets indicate the standard error. **=p<0.01 compared to the values obtained with injections of saline. The results show that direct intrastriatal administration of $D_2$ antisense produced a dose-related inhibition of the rotational response induced by the $D_2$ dopamine receptor against quinpirole.

Figure 9:
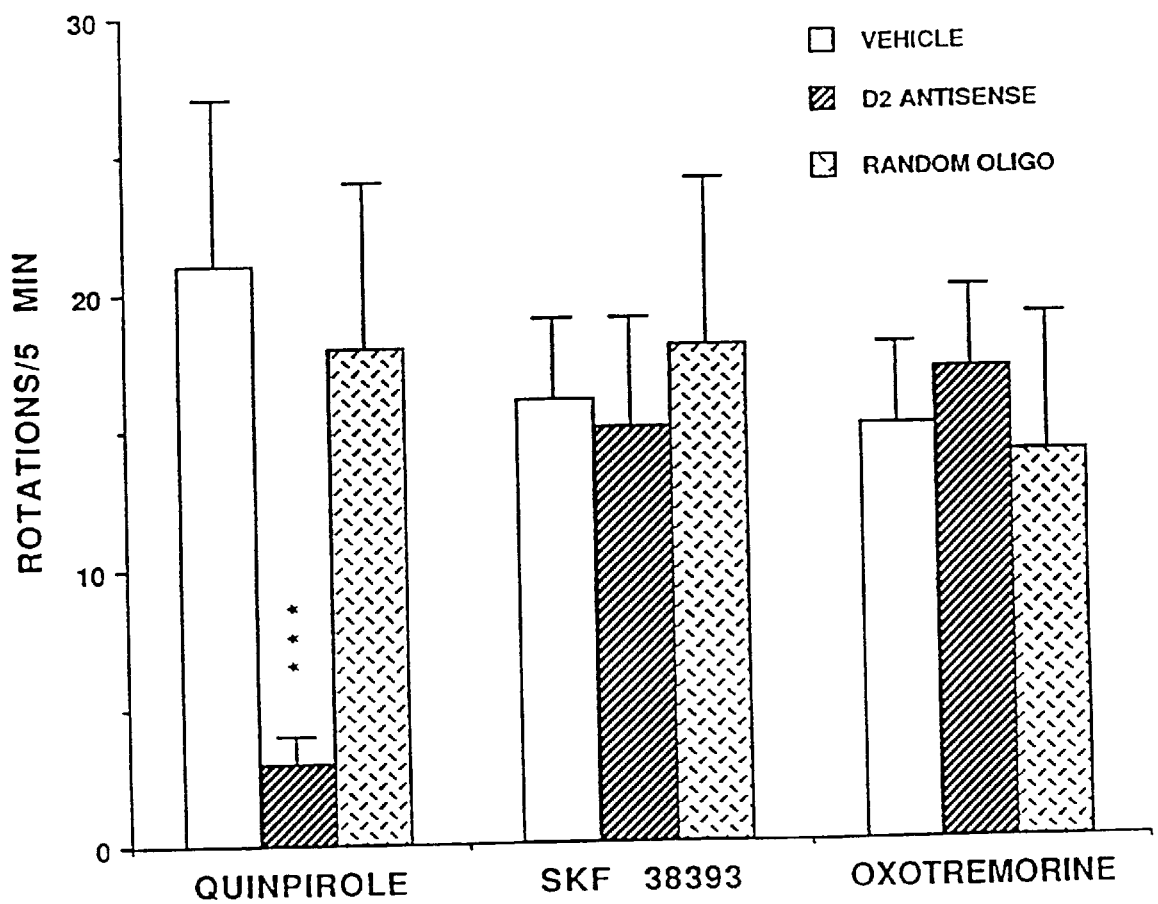
FIG. 9 is a graph showing that direct intrastriatal administration of a $D_2$ antisense oligonucleotide, but not an oligonucleotide of random sequence, inhibits rotational behavior in unilaterally 6-OHDA-lesioned mice induced by quinpirole, but does not inhibit rotational behavior induced by the $D_1$ agonist, SKF-38393, or the cholinergic agonist, oxotremorine.

Next, a comparison was made of the effect of direct intrastriatal administration of $D_2$ S-oligo on rotational behavior induced by quinpirole, SKF 38393 and oxotremorine in 6-OHDA-lesioned mice. Mice with unilateral intrastriatal lesions induced by 6-OHDA were administered intrastriatal injections of vehicle (2 μl of artificial), $D_2$ antisense (2.5 nmol/2 μl) or random oligo (2.5 nmol/2 μl) twice daily for two days. Mice were challenged with the $D_2$ dopamine receptor agonist quinpirole (5 μmol/kg, s.c.), the $D_1$ dopamine receptor agonist SKF 38393 (80 μmol/kg, s.c.) or the muscarinic cholinergic receptor agonist oxotremorine (5 μmol/kg, s.c.) 10 hr after the last injection of vehicle or oligomers, and rotational behavior was assessed. Results are shown in FIG. 9. Each point represents the mean value from 5–14 mice. The rotational score in response to challenge injections of vehicle was zero. Vertical brackets indicate the standard error. ***=p<0.001 compared with vehicle- or random oligo-treated mice. The results show that direct intrastriatal administration of $D_2$ antisense inhibited the rotational response to the $D_2$ dopamine receptor agonist quinpirole but not that to the $D_1$ dopamine receptor agonist SKF 38393 or to the muscarinic cholinergic receptor agonist oxotremorine.

EXAMPLE 2

Inhibition in Unlesioned and 6-Hydroxydopamine Lesioned Mice of SKF 38393-Induced Behaviors by Administration of an Oligonucleotide Antisense to the $D_1$ Dopamine Receptor mRNA Two behavioral analyses were used to determine the effectiveness and specificity of an oligonucleotide antisense to the $D_1$ dopamine receptor mRNA. First, as described in Example 1, mice rendered supersensitive by lesioning with 6-OHDA exhibit rotational behavior that can be induced by the $D_1$ agonist SKF 38393, as well as by the $D_2$ agonist quinpirole. This SKF 38393-induced rotational behavior in 6-OHDA lesioned mice was utilized as one behavioral system for analysis of the $D_1$ antisense oligonucleotide. In addition, unlesioned mice, when challenged with acute doses of SKF 38393 exhibit a grooming behavior associated with stimulation by SKF 38393 and other $D_1$ agonists. See Weiss et al., 1989, supra. SKF 38393-induced grooming behavior in unlesioned mice was also used as a behavioral system for evaluating the effectiveness of the $D_1$ antisense oligonucleotides.

The methods and reagents used in the analysis of the $D_1$ antisense oligonucleotide were the same as described for the $D_2$ antisense oligonucleotide in Example 1. Based on the sequence for mouse $D_1$ dopamine receptor mRNA, a 20-mer phosphorthioate oligodeoxynucleotide (referred to herein as $D_1$ antisense or $D_1$ S-oligo) antisense to a region surrounding the initiation codon (−10 to +10) of the mouse $D_1$ dopamine receptor mRNA: 5'-GTTAGGAGCCATCTTCCAGA-3' (Sequence ID No.

2), was designed and synthesized. A 20-mer phosphorothioate oligodeoxynucleotide having a random sequence (referred to as random S-oligo or random oligo), 5'-ATACTTCACGCCGATGGTGA-3' (Sequence ID No. 13), was used as a control. Oligonucleotides were synthesized as described in Example 1.

Figure 10:
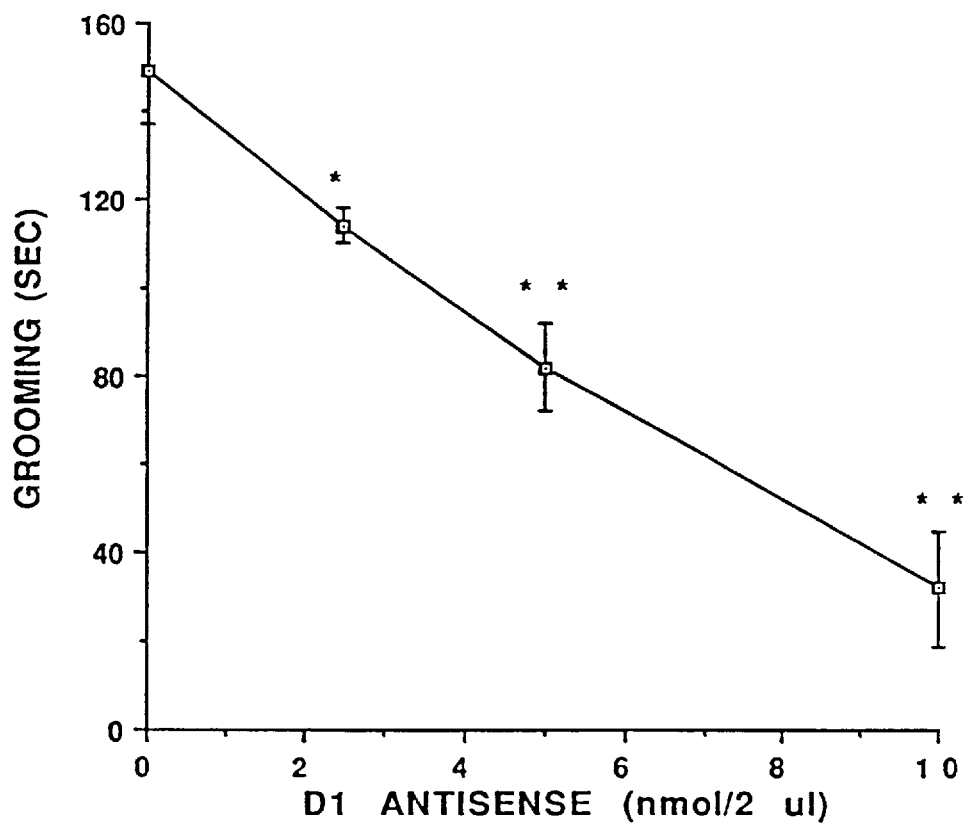
FIG. 10 is a graph showing the concentration-dependent inhibition of SKF-38393-induced grooming behavior resulting from administration of a $D_1$ antisense oligonucleotide.

In one procedure, the effect and concentration-dependence of $D_1$ S-oligo on SKF 38393-induced grooming behavior was analyzed. Mice were administered intraventricular injections of various doses of the $D_1$ antisense every 12 hr for three injections. Grooming behavior induced by acute challenge injections of the $D_1$ dopamine receptor agonist SKF 38393 (40 µmol/kg,s.c.) was measured 10 hr after the third injection of $D_1$ antisense. Results are shown in FIG. 10. The values shown represent the increase in grooming score over that produced by acute challenge injections of saline. The control grooming score value was 40 sec. Each point represents the mean value from 4 mice. Vertical brackets indicate the standard error. *=p<0.05; **=p<0.01 compared to the values obtained with saline. The results show that $D_1$ antisense produced a dose-related inhibition of grooming behavior in response to the $D_1$ dopamine receptor agonist SKF 38393.

Figure 11:
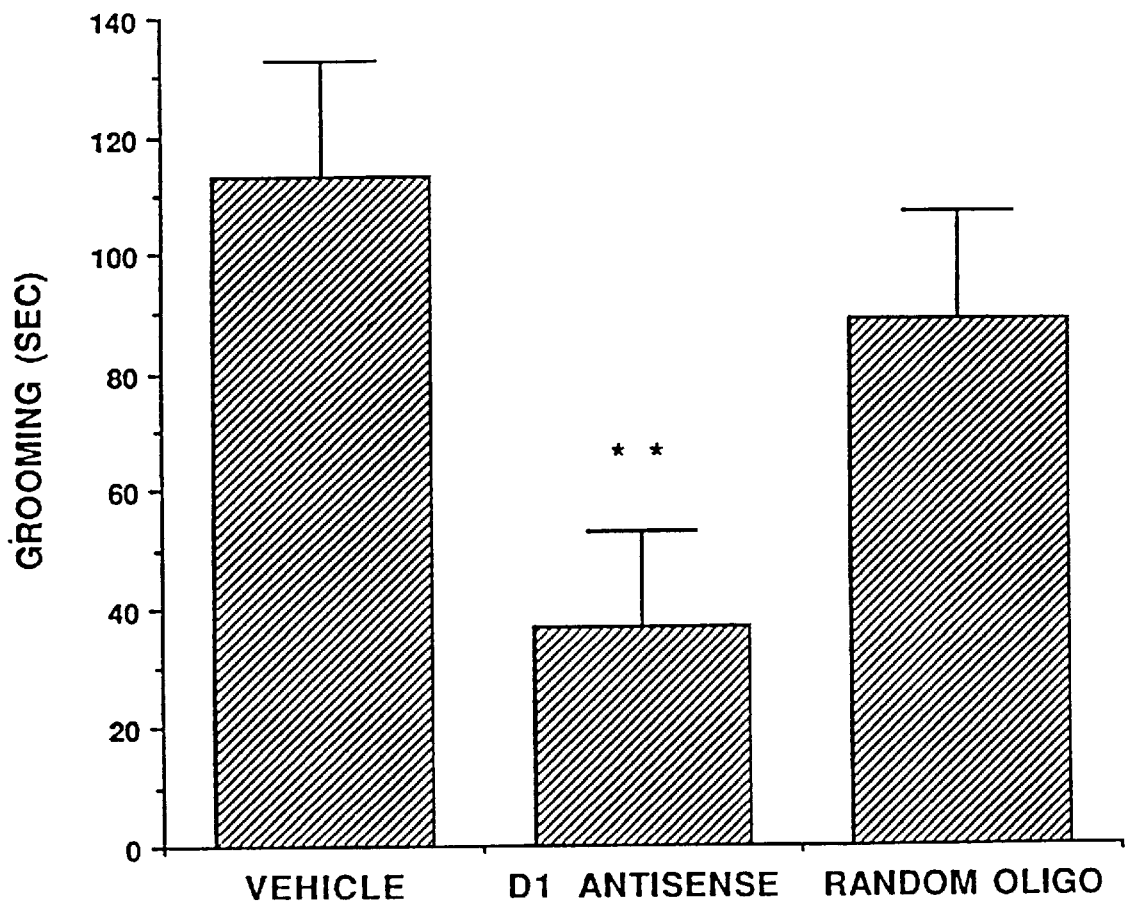
FIG. 11 is a graph showing the inhibition of SKF-38393-induced grooming behavior in mice resulting from administration of a $D_1$ antisense oligonucleotide and the absence of such inhibition upon treatment with a random sequence oligonucleotide.

To compare the effect of $D_1$ S-oligo with the random oligonucleotide, mice were administered intraventricular injections of vehicle (2 µl of artificial CSF), $D_1$ S-oligo (2.5 µmol/2 µl) or random oligo (2.5 µmol/2 µl) twice daily for 7 days. Grooming behavior induced by acute injections of SKF 38393 (40 µmol/kg,s.c.) was determined 10 hr after the last injection of vehicle or oligomers. The control grooming score in repsonse to acute challenge injections of saline was 40 sec. These results are shown in FIG. 11. The values shown represent the increase in grooming score over control values. Each point represents the mean value from 5 mice. Vertical brackets indicate the standard error. **=p<0.01 compared to vehicle-treated mice. The results show that treatment of mice with $D_1$ antisense inhibited the grooming behavior induced by the $D_1$ dopamine receptor against SKF 38393. By contrast, similar injections of random oligo failed to produce significant inhibition of SKF 38393-induced grooming behavior.

Figure 12:
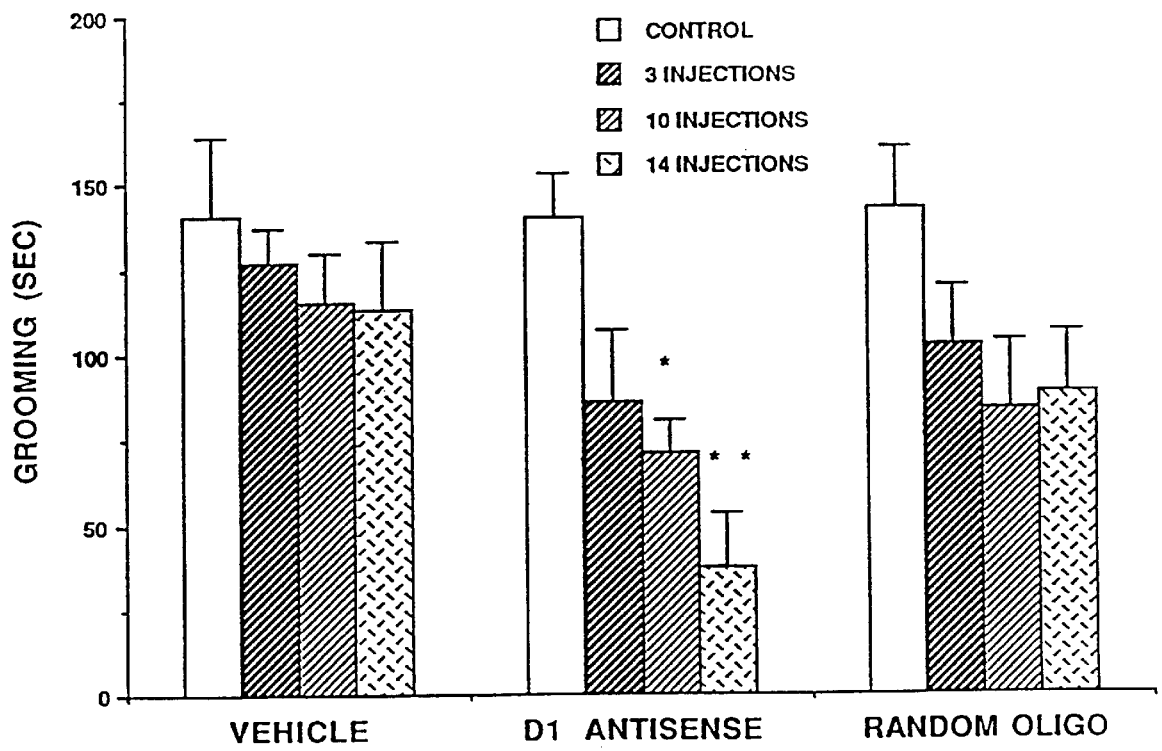
FIG. 12 is a graph showing the effect of repeated injections of a $D_1$ antisense oligonucleotide on SKF-38393-induced grooming behavior in mice.

The effect of repeated injections of $D_1$ antisense on SKF 38393-induced grooming behavior was also evaluated. Mice were administered from 1–14 intraventricular injections of vehicle (21 µl of artificial CSF), $D_1$ antisense (2.5 nmol/2 µl) or random oligo (2.5 nmol/2 µl). Injections were made twice daily for 7 days. Grooming behavior induced by challenge injections of SKF 38393 was determined 10 hr after each injection of vehicle or oligomer. Results are shown in FIG. 12. Each point represents the mean value from 5 mice. Vertical brackets indicate the standard error. *=p<0.05; **=p<0.01 compared to vehicle-treated mice. The results show that statistically significant inhibition of SKF 38393-induced grooming behavior was seen after 10 injections of $D_1$ antisense, and still greater inhibition was seen after 14 injections of $D_1$ antisense. The random oligo failed to produce significant inhibition of SKF 38393-induced grooming behavior at any time point studied.

Figure 13B:
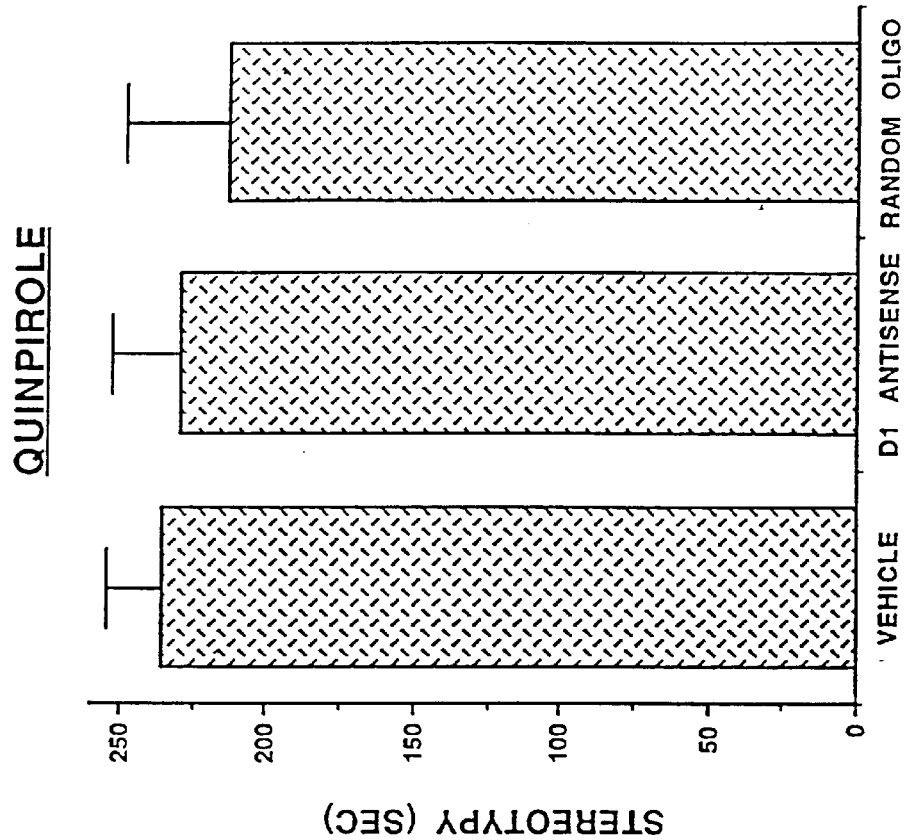
FIGS. 13A and 13B are a graph showing the inhibition by a $D_1$ antisense oligonucleotide, but not by an oligonucleotide of random sequence, of grooming behavior induced by SKF-38393, and the absence of such inhibition when stereotypy behavior was induced by the $D_2$ agonist, quinpirole.
Figure 13A:
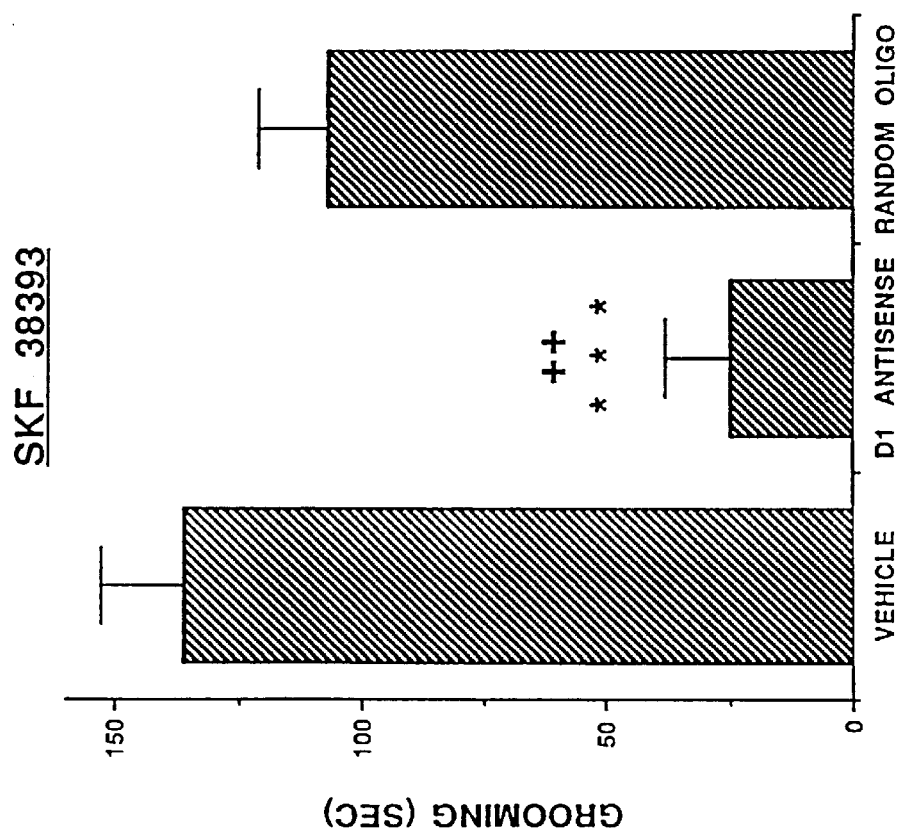

To demonstrate the specificity of the $D_1$ antisense oligonucleotide for $D_1$ receptor mRNA, the following procedure was performed. Mice were administered intraventricular injections of vehicle (2 µl of artificial CSF), $D_1$ antisense (2.5 nmol/2 µl) or random oligo (2.5 nmol/2 µl) twice daily for 6 days. Grooming behavior induced by SKF 38393 (80 µmol/kg,s.c.) and stereotyped behavior induced by quinpirole (20 µmol/kg,s.c.) were measured 10 hr after the last injection of vehicle or oligomer. Results are shown in FIG. 13. Each bar represents the mean value from 5 mice. Vertical brackets indicate the standard error. ++=p<0.01 compared to random oligo-treated mice. ***=p<0.01 compared to vehicle-treated mice. The results show that $D_1$ antisense inhibited the grooming behavior induced by the $D_1$ dopamine receptor agonist SKF 38393 but did not inhibit the stereotyped behavior induced by the $D_2$ dopamine receptor agonist quinpirole.

Figure 14:
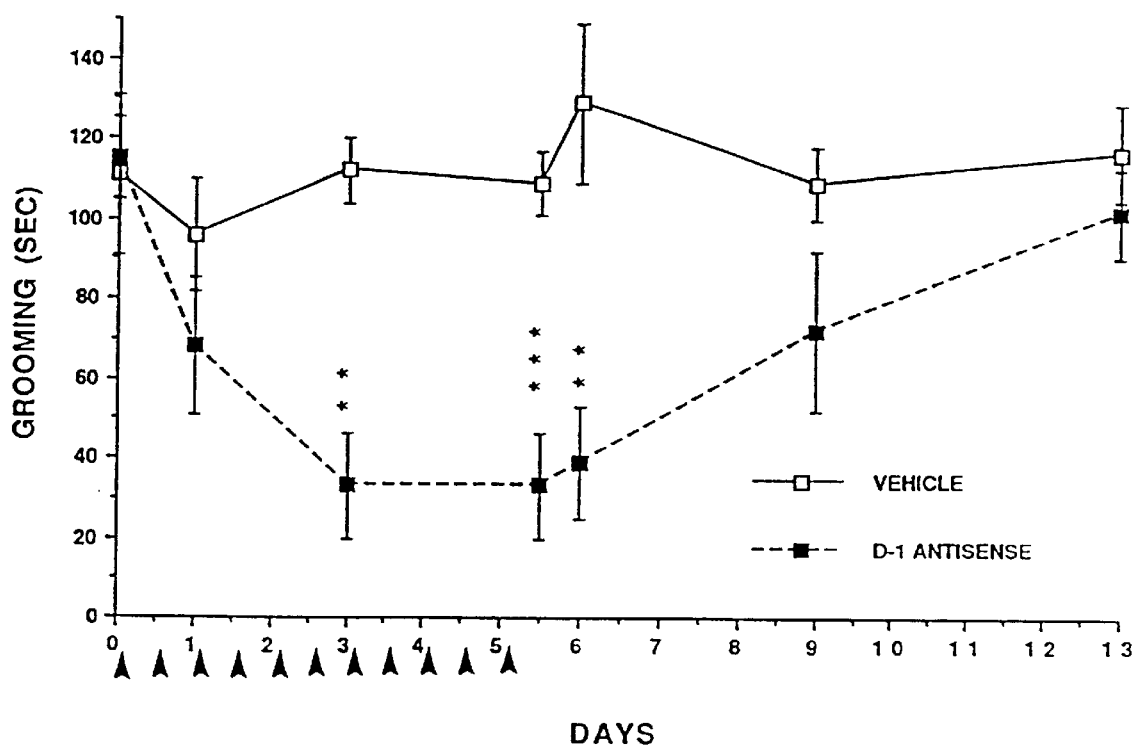
FIG. 14 is a graph showing the rate of recovery from $D_1$ antisense oligonucleotide inhibition of SKF-38393-induced grooming behavior in mice after cessation of $D_1$ antisense treatment.

In another procedure, the rate of recovery of SKF 38393-induced grooming behavior was measured after cessation of $D_1$ antisense treatment. Mice were administered intraventricular injections of vehicle (2 µl of artificial CSF), or $D_1$ antisense (2.5 nmol/2 µl) at 12 hr intervals (shown by the arrow heads in FIG. 14). Grooming behavior induced by SKF 38393 (40 µmol/kg,s.c.) was measured 10 hr after the second and sixth injection of vehicle or $D_1$ antisense, and at 12, 24, 96 and 192 hr after the last injection of vehicle or $D_1$ antisense. Results are shown in FIG. 14. Each point represents the mean value from 5 mice. Vertical brackets indicate the standard error. =p<0.0; *=p<0.001 compared to vehicle-treated mice. The results show that repeated injections of $D_1$ antisense significantly reduced the grooming behavior induced by the $D_1$ dopamine receptor agonist SKF 38393. At 24 hr after the last injection of $D_1$ antisense there was still a highly significant inhibition of the action of SKF 38393. However, by 4 days after the last injection of $D_1$ antisense, the effects of SKF 38393 had returned to that found in vehicle-treated animals, results that demonstrate the reversible nature of the inhibition.

Figure 15:
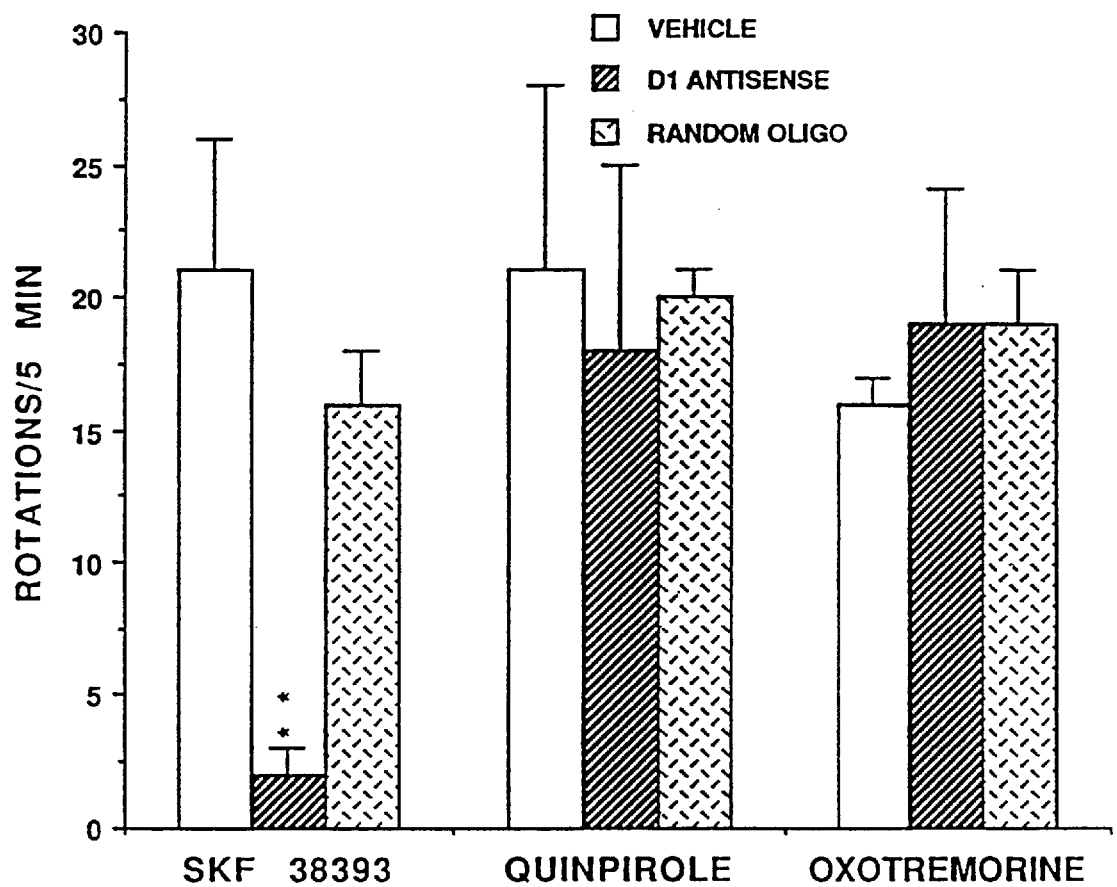
FIG. 15 is a graph showing the inhibition by a $D_1$ antisense oligonucleotide, but not by an oligonucleotide of random sequence, of rotational behavior in unilaterally 6-OHDA-lesioned mice induced by SKF-38393, and the absence of such inhibition when rotational behavior was induced by the $D_2$ agonist, quinpirole, or the cholinergic agonist, oxotremorine.

In a procedure utilizing the rotational behavioral model, a comparison was made of the effect of $D_1$ antisense on rotational behavior induced by SKF 38393, quinpirole and oxotremorine in 6-hydroxydopamine (6-OHDA) lesioned mice. Mice with unilateral intrastriatal lesions induced by 6-OHDA were administered intraventricular injections of vehicle (2 µl of artificial CSF), $D_1$ antisense (2.5 nmol/2 µl) or random oligo (2.5 nmol/2 µl) twice daily for 2 days. Mice were challenged with the $D_1$ dopamine receptor agonist SKF 38393 (40 µmol/kg,s.c.), the $D_2$ dopamine receptor agonist quinpirole (5 µmol/kg,s.c.) or the muscarinic cholinergic receptor agonist oxotremorine (5 µmol/kg, s.c.) 10 hr after the last injection of vehicle or oligomer, and rotational behavior was assessed. Results are shown in FIG. 15. The rotational score in response to challenge injections of vehicle was zero. Each point represents the mean value from 3–4 mice. Vertical brackets indicate the standard error. **=p<0.01 compared to vehicle or random oligo-treated mice. The results show that the $D_1$ antisense inhibited the rotational response to the $D_1$ dopamine receptor agonist SKF 38393 but not that to the $D_2$ dopamine receptor agonist quinpirole or to the muscarinic cholinergic receptor agonist oxotremorine.

Figure 16C:
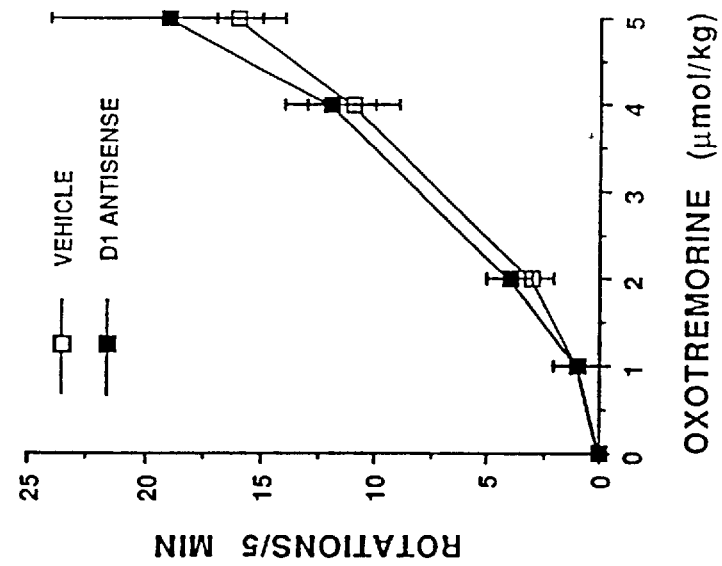
FIGS. 16A, 16B, and 16C are a set of graphs showing the effect of a $D_1$ antisense oligonucleotide on rotational behavior induced by varying doses of SKF-38393 (Graph A), quinpirole (Graph B), and oxotremorine (Graph C), in unilaterally 6-OHDA-lesioned mice.
Figure 16B:
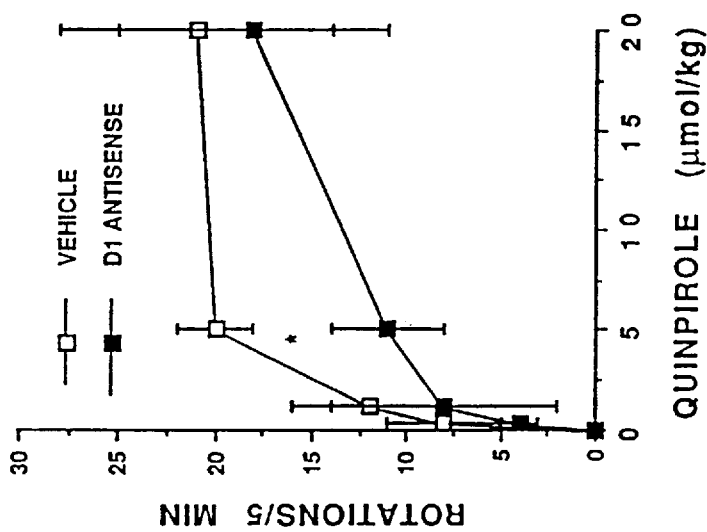
Figure 16A:
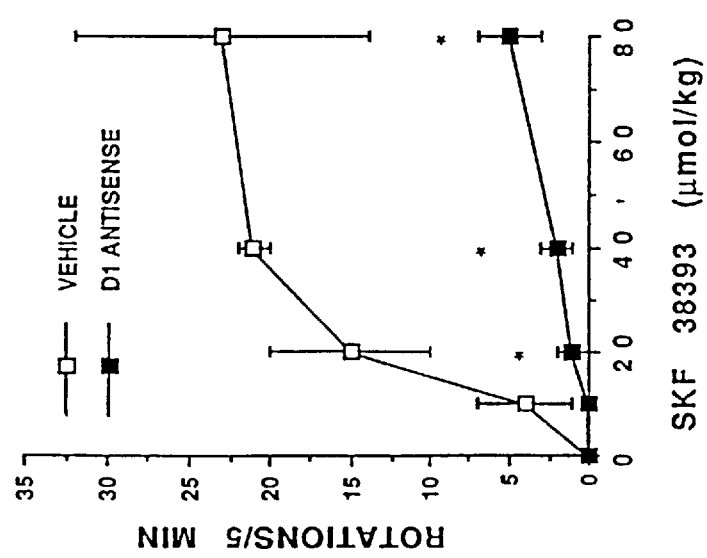

Another comparison was made to determine the effect of $D_1$ antisense on rotational behavior induced by varying doses of SKF 38393, quinpirole and oxotremorine in 6-hydroxydopamine (6-OHDA) lesioned mice. Mice with unilateral intrastriatal lesions induced by 6-OHDA were administered intraventricular injections of $D_1$ antisense (2.5 nmol/2 µl) or vehicle (2 µl of artificial CSF). Injections were made twice daily for four days. As shown in FIG. 16, mice were challenged with varying doses of SKF 38393 (A), quinpirole (B) and oxotremorine (C) at 10 hr after the last injection of vehicle or $D_1$ antisense. Each point represents the mean value from 3–4 mice. Vertical brackets indicate the standard error. *=p<0.05 compared to vehicle-treated mice. The results show that $D_1$ antisense significantly inhibited rotational behavior induced by the $D_1$ dopamine receptor agonist SKF 38393, even when given at doses more than 5 times its $ED_{50}$. By contrast, there was only a slight inhibition of rotational response induced by the $D_2$ dopamine receptor agonist quinpirole, and this inhibition was no longer evident when the mice were challenged with higher doses of quinpirole. $D_1$ antisense treatment failed to alter the response to any dose of quinpirole (FIG. 16B) or oxotremorine (FIG. 16C). These experiments demonstrate the great selectivity by which the $D_1$ S-oligo inhibited $D_1$-mediated responses.

Figure 17:
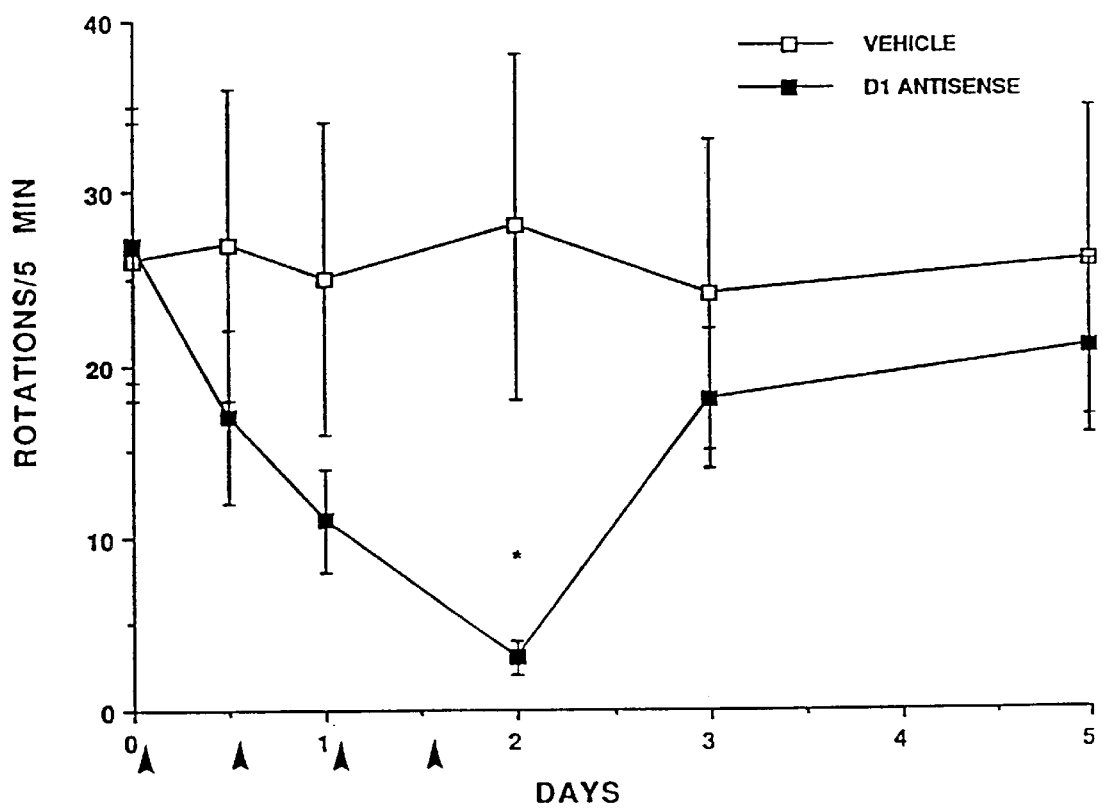
FIG. 17 is a graph showing the rate of recovery from $D_1$ antisense oligonucleotide inhibition of SKF-38393-induced rotational behavior in unilaterally 6-OHDA-lesioned mice.

The rate of recovery of SKF 38393-induced rotational behavior after cessation of $D_1$ antisense treatment was also measured. Mice with unilateral intrastriatal lesions induced by 6-OHDA were administered intraventricular injections of vehicle (2 μl of artificial CSF), or $D_1$ antisense (2.5 nmol/2 μl) four times at 12 hr intervals (shown by the arrow heads). Rotational behavior induced by the $D_1$ dopamine receptor agonist SKF 38393 (40 μmol/kg,s.c.) was measured 10 hr after the first and second injections of vehicle or $D_1$ antisense, and at 12, 36 and 84 hr after the last injection of vehicle or $D_1$ antisense. Results are shown in FIG. 17. Each point represents the mean value from 4 mice. Vertical brackets indicate the standard error. *=$p<0.05$ compared to vehicle-treated mice. The results show that at 12 hr after the last injection of $D_1$ dopamine there was a significant inhibition of rotational behavior induced by the $D_1$ dopamine receptor agonist SKF 38393. However, at 36 hr after the last injection of $D_1$ antisense, the effect of SKF 38393 was similar to that found in vehicle-treated animals.

The present invention is not limited to the embodiments specifically described and exemplified above, but is capable of variation and modification without departure from the scope of the appended claims.

What is claimed is:

1. A method of inhibiting production of a pre-determined dopamine receptor in a human cell, said method comprising:
    a) providing an antisense oligonucleotide which hybridizes to the expression-controlling sequence comprising the translational start site of a nucleic acid that encodes said predetermined dopamine receptor, said oligonucleotide consisting of a sequence selected from the group consisting of SEQ ID NO: 3, SEQ ID NO: 4, SEQ ID NO: 5, SEQ ID NO: 7 and SEQ ID NO: 8; and
    b) contacting said human cell with said antisense oligonucleotide under conditions whereby said antisense oligonucleotide enters cells producing said dopamine receptor and hybridizes with said expression-controlling sequence of said nucleic acid encoding said predetermined dopamine receptor to inhibit production of said dopamine receptor in said human cell.

2. A method according to claim 1, wherein said predetermined dopamine receptor is a $D_1$ receptor, and said antisense oligonucleotide consists of the sequence defined by SEQ ID NO: 4.

3. A method according to claim 1, wherein said predetermined dopamine receptor is a $D_1$ receptor, and said antisense oligonucleotide consists of the sequence defined by SEQ ID NO: 3.

4. A method according to claim 1, wherein said predetermined dopamine receptor is a $D_3$ receptor, and said antisense oligonucleotide consists of the sequence defined by SEQ ID NO: 5.

5. A method according to claim 1, wherein said predetermined receptor is a $D_4$ receptor, and said antisense oligonucleotide consists of the sequence defined by SEQ ID NO: 7.

6. A method according to claim 1, wherein said predetermined receptor is a $D_5$ receptor, and said antisense oligonucleotide consists of the sequence defined by SEQ ID NO: 8.

7. A method according to claim 1, wherein said antisense oligonucleotide is a modified oligonucleotide analog, said modification being selected selected from the group consisting of phosphorothioate oligodeoxynucleotide analogs or methylphosphonate oligodeoxynucleotide analogs.

8. An antisense oligonucleotide which hybridizes after entry into a human cell, with a translational start site of a nucleic acid that encodes a dopamine receptor, said antisense oligonucleotide consisting of a sequence selected from the group consisting of SEQ ID NO: 3, SEQ ID NO: 4, SEQ ID NO: 5, SEQ ID NO: 7, and SEQ ID NO: 8.

9. A modified antisense oligonucleotide analog as claimed in claim 8, wherein said modification is selected selected from the group consisting of phosphorothioate oligodeoxynucleotide analogs or methylphosphonate oligodeoxynucleotide analogs.

10. A method of inhibiting synthesis of a pre-determined dopamine receptor in a rodent cell, said method comprising:
    a) providing an antisense oligonucleotide which hybridizes with the expression-controlling sequence comprising a translational start site of a nucleic acid that encodes said pre-determined dopamine receptor, said oligonucleotide consisting of a sequence selected from the group consisting of SEQ ID NO: 1, SEQ ID NO: 2, and SEQ ID NO: 6; and
    b) administering said antisense oligonucleotide to said rodent cell under conditions whereby said antisense oligonucleotide enters cells expressing said dopamine receptor and specifically hybridizes with said expression-controlling sequence of said nucleic acid encoding said dopamine receptor, in an amount sufficient to inhibit production of said dopamine receptor.

11. A method according to claim 10, wherein said predetermined dopamine receptor is a $D_2$ receptor, and said antisense oligonucleotide consists of the sequence defined by SEQ ID NO: 1.

12. A method according to claim 10, wherein said predetermined dopamine receptor is a $D_1$ receptor, and said antisense oligonucleotide consists of the sequence defined by SEQ ID NO: 2.

13. A method according to claim 10, wherein said predetermined dopamine receptor is a $D_3$ receptor, and said antisense oligonucleotide consists of the sequence defined by SEQ ID NO: 6.

14. A method according to claim 10, wherein said antisense oligonucleotide is a modified antisense oligonucleotide analog, said modification being selected from the group consisting of phosphorothioate oligodeoxynucleotide analogs or methylphosphonate oligodeoxynucleotide analogs.

15. A method according to claim 10, wherein said antisense oligonucleotide is a phosphorothioate oligodeoxynucleotide.

16. An antisense oligonucleotide which hybridizes after entry into a rodent cell, with a translational start site of a nucleic acid that encodes a dopamine receptor, said antisense oligonucleotide consisting of a sequence selected from the group consisting of SEQ ID NO: 1, SEQ ID NO: 2 and SEQ ID NO: 6.

17. An antisense oligonucleotide as claimed in claim 16, wherein said antisense oligonucleotide is a phosphorothioate oligodeoxynucleotide.

18. An antisense oligonucleotide preparation comprising an antisense oligonucleotide which hybridizes to the translational start site of a nucleic acid encoding a dopamine receptor, said antisense oligonucleotide consisting of a sequence selected from the group consisting of SEQ ID NO: 1, SEQ ID NO: 2 and SEQ ID NO: 6 and further being disposed within a biologically compatible medium.

19. A preparation according to claim 18, wherein said antisense oligonucleotide is a phosphorothioate oligodeoxynucleotide.

20. A preparation according to claim 18, wherein said biologically compatible medium contains at least one agent for improving membrane permeability of said antisense oligonucleotide.

21. A preparation according to claim 20, wherein said biologically compatible medium contains at least one targeting agent for effecting delivery of said antisense oligonucleotide analog to said cells expressing said dopamine receptor.

22. A preparation according to claim 21, wherein said at least one targeting agent comprises a liposome having binding affinity for said cells expressing said dopamine receptor, and said antisense oligonucleotide is encapsulated within said liposome.

23. An antisense oligonucleotide analog for inhibiting D2 dopamine receptor agonist-induced rotational behavior in rodents, when administered by intraventricular or intrastriatal injection, said antisense oligonucleotide analog being diffusible across a biological membrane and consisting of the sequence of SEQ. ID No. 1, said antisense oligonucleotide analog specifically hybridizing to a nucleotide sequence comprising a translation start site of mRNA encoding said $D_2$ dopamine receptor, in an amount sufficient to inhibit the production of said $D_2$ dopamine receptor.

24. An antisense oligonucleotide analog for inhibiting $D_1$ dopamine receptor agonist-induced behaviors in rodents when administered by intraventricular injection, said antisense oligonucleotide analog having the sequence of SEQ. ID No. 2 and being diffusible across a biological membrane, said antisense oligonucleotide analog specifically hybridizing with a nucleotide sequence comprising a translation start site of mRNA encoding said $D_1$ dopamine receptor in an amount sufficient to inhibit production of said $D_1$ dopamine receptor.

25. A method of determining if a test compound is a specific regulator of a pre-determined dopamine receptor subtype, which comprises:

a) providing in vitro cells producing said pre-determined dopamine receptor subtype, said cells having at least one detectable biological function that is related to a response of said pre-determined dopamine receptor subtype caused by said specific regulator;

b) contacting said in vitro cultured cells with an antisense oligonucleotide which hybridizes to an expression control sequence of a nucleic acid that encodes said pre-determined dopamine receptor subtype, said antisense oligonucleotide consisting of a sequence selected from the group of sequences consisting of SEQ ID NO:1, SEQ ID NO:2, SEQ ID NO:3, SEQ ID NO:4, SEQ ID NO:5, SEQ ID NO: 6, SEQ ID NO: 7, SEQ ID NO: 8, SEQ ID NO: 9, SEQ ID NO:10, and SEQ ID NO: 11;

c) pre-treating a quantity of said in vitro cultured cells with said antisense oligonucleotide in an amount sufficient to inhibit production of said specific dopamine receptor subtype under conditions whereby said antisense oligonucleotide enters said in vitro cultured cells and hybridizes to said expression-controlling sequence;

d) exposing said pre-treated cells and an equivalent quantity of non pre-treated cells to said test compound under conditions and in an amount sufficient to alter said regulatory effect of said test compound if any, on said dopamine receptor subtype;

e) detecting a change in said biological function, if any, in said pre-treated cells and said non pre-treated in vitro cultured cells resulting from said exposure to said test compound; and f) comparing said pre-treated cells with said non pre-treated cells to determine whether or not said control of expression of said specific dopamine receptor subtype by said antisense oligonucleotide in said pre-treated cells alleviates said change in said related biological function, if any, exerted by said test compound, said alleviation being indicative that said test compound is a specific regulator of said pre-determined dopamine receptor subtype.

26. A method according to claim 25, wherein said specific dopamine receptor subtype is selected from the group consisting of $D_1$, $D_2$, $D_3$, $D_4$ and $D_5$.

27. A method according to claim 25, wherein said biological function is selected from the group consisting of adenylate cyclase activity and release of acetylcholine from said cells.

* * * * *

SEQUENCE LISTING ( 1 ) GENERAL INFORMATION:

( i i i ) NUMBER OF SEQUENCES: 13

( 2 ) INFORMATION FOR SEQ ID NO:1:

( i ) SEQUENCE CHARACTERISTICS:
        ( A ) LENGTH: 20 base pairs
        ( B ) TYPE: nucleic acid
        ( C ) STRANDEDNESS: single
        ( D ) TOPOLOGY: linear ( i i ) MOLECULE TYPE: cDNA to mRNA ( i i i ) HYPOTHETICAL: NO ( i v ) ANTI-SENSE: YES ( x i ) SEQUENCE DESCRIPTION: SEQ ID NO:1:

GTGGATCCAT TGGGGCAGTG        20

( 2 ) INFORMATION FOR SEQ ID NO:2:

( i ) SEQUENCE CHARACTERISTICS:
        ( A ) LENGTH: 20 base pairs
        ( B ) TYPE: nucleic acid
        ( C ) STRANDEDNESS: single
        ( D ) TOPOLOGY: linear ( i i ) MOLECULE TYPE: cDNA to mRNA ( i i i ) HYPOTHETICAL: NO ( i v ) ANTI-SENSE: YES ( x i ) SEQUENCE DESCRIPTION: SEQ ID NO:2:

GTTAGGAGCC ATCTTCCAGA        20

( 2 ) INFORMATION FOR SEQ ID NO:3:

( i ) SEQUENCE CHARACTERISTICS:
        ( A ) LENGTH: 20 base pairs
        ( B ) TYPE: nucleic acid
        ( C ) STRANDEDNESS: single
        ( D ) TOPOLOGY: linear ( i i ) MOLECULE TYPE: cDNA to mRNA ( i i i ) HYPOTHETICAL: NO ( i v ) ANTI-SENSE: YES ( x i ) SEQUENCE DESCRIPTION: SEQ ID NO:3:

GAGTCCTCAT CTTCCTAAGA 20

( 2 ) INFORMATION FOR SEQ ID NO:4:

( i ) SEQUENCE CHARACTERISTICS:
        ( A ) LENGTH: 20 base pairs
        ( B ) TYPE: nucleic acid
        ( C ) STRANDEDNESS: single
        ( D ) TOPOLOGY: linear ( i i ) MOLECULE TYPE: cDNA to mRNA ( i i i ) HYPOTHETICAL: NO ( i v ) ANTI-SENSE: YES ( x i ) SEQUENCE DESCRIPTION: SEQ ID NO:4:

GTGGATCCAT CAGGGCGGTG 20

( 2 ) INFORMATION FOR SEQ ID NO:5:

( i ) SEQUENCE CHARACTERISTICS:
        ( A ) LENGTH: 20 base pairs
        ( B ) TYPE: nucleic acid
        ( C ) STRANDEDNESS: single
        ( D ) TOPOLOGY: linear ( i i ) MOLECULE TYPE: cDNA to mRNA ( i i i ) HYPOTHETICAL: NO ( i v ) ANTI-SENSE: YES ( x i ) SEQUENCE DESCRIPTION: SEQ ID NO:5:

CTCAGAGATG CCATAGCCCA 20

( 2 ) INFORMATION FOR SEQ ID NO:6:

( i ) SEQUENCE CHARACTERISTICS:
        ( A ) LENGTH: 20 base pairs
        ( B ) TYPE: nucleic acid
        ( C ) STRANDEDNESS: single
        ( D ) TOPOLOGY: linear ( i i ) MOLECULE TYPE: cDNA to mRNA ( i i i ) HYPOTHETICAL: NO ( i v ) ANTI-SENSE: YES ( x i ) SEQUENCE DESCRIPTION: SEQ ID NO:6:

GAGGTGCCAT GGCCCACACA 20

( 2 ) INFORMATION FOR SEQ ID NO:7:

( i ) SEQUENCE CHARACTERISTICS:
        ( A ) LENGTH: 20 base pairs
        ( B ) TYPE: nucleic acid
        ( C ) STRANDEDNESS: single
        ( D ) TOPOLOGY: linear ( i i ) MOLECULE TYPE: cDNA to mRNA ( i i i ) HYPOTHETICAL: NO ( i v ) ANTI-SENSE: YES ( x i ) SEQUENCE DESCRIPTION: SEQ ID NO:7:

GGTTCCCCAT GGCGCGCCCG 20

( 2 ) INFORMATION FOR SEQ ID NO:8:

( i ) SEQUENCE CHARACTERISTICS:
           ( A ) LENGTH: 20 base pairs
           ( B ) TYPE: nucleic acid
           ( C ) STRANDEDNESS: single
           ( D ) TOPOLOGY: linear ( i i ) MOLECULE TYPE: cDNA to mRNA ( i i i ) HYPOTHETICAL: NO ( i v ) ANTI-SENSE: YES ( x i ) SEQUENCE DESCRIPTION: SEQ ID NO:8:

GCGGCAGCAT TTCGGGCTGG                                                2 0

( 2 ) INFORMATION FOR SEQ ID NO:9:

( i ) SEQUENCE CHARACTERISTICS:
           ( A ) LENGTH: 20 base pairs
           ( B ) TYPE: nucleic acid
           ( C ) STRANDEDNESS: single
           ( D ) TOPOLOGY: linear ( i i ) MOLECULE TYPE: cDNA to mRNA ( i i i ) HYPOTHETICAL: NO ( i v ) ANTI-SENSE: YES ( x i ) SEQUENCE DESCRIPTION: SEQ ID NO:9:

CTCCAAACGC CTTAAAAAGC                                                2 0

( 2 ) INFORMATION FOR SEQ ID NO:10:

( i ) SEQUENCE CHARACTERISTICS:
           ( A ) LENGTH: 20 base pairs
           ( B ) TYPE: nucleic acid
           ( C ) STRANDEDNESS: single
           ( D ) TOPOLOGY: linear ( i i ) MOLECULE TYPE: cDNA to mRNA ( i i i ) HYPOTHETICAL: NO ( i v ) ANTI-SENSE: YES ( x i ) SEQUENCE DESCRIPTION: SEQ ID NO:10:

CACCTACCTC CATCTCCAGC                                                2 0

( 2 ) INFORMATION FOR SEQ ID NO:11:

( i ) SEQUENCE CHARACTERISTICS:
           ( A ) LENGTH: 20 base pairs
           ( B ) TYPE: nucleic acid
           ( C ) STRANDEDNESS: single
           ( D ) TOPOLOGY: linear ( i i ) MOLECULE TYPE: cDNA to mRNA ( i i i ) HYPOTHETICAL: NO ( i v ) ANTI-SENSE: YES ( x i ) SEQUENCE DESCRIPTION: SEQ ID NO:11:

CGCGGCTCAC CTCGGAGTAG                                                2 0

( 2 ) INFORMATION FOR SEQ ID NO:12:

(i) SEQUENCE CHARACTERISTICS:
            (A) LENGTH: 20 base pairs
            (B) TYPE: nucleic acid
            (C) STRANDEDNESS: single
            (D) TOPOLOGY: linear (ii) MOLECULE TYPE: cDNA to mRNA (iii) HYPOTHETICAL: NO (iv) ANTI-SENSE: YES (xi) SEQUENCE DESCRIPTION: SEQ ID NO:12:

GTGCTTGACG CGGATGGTGA                                                                                      20

(2) INFORMATION FOR SEQ ID NO:13:

(i) SEQUENCE CHARACTERISTICS:
            (A) LENGTH: 20 base pairs
            (B) TYPE: nucleic acid
            (C) STRANDEDNESS: single
            (D) TOPOLOGY: linear (ii) MOLECULE TYPE: cDNA to mRNA (iii) HYPOTHETICAL: NO (iv) ANTI-SENSE: YES (xi) SEQUENCE DESCRIPTION: SEQ ID NO:13:

AGACTTCACG CCGATGGTGA                                                                                      20